United States Patent
Thibault et al.

(10) Patent No.: US 12,274,577 B2
(45) Date of Patent: Apr. 15, 2025

(54) SYSTEMS AND METHODS FOR COMPUTED TOMOGRAPHY

(71) Applicant: GE Precision Healthcare LLC, Wauwatosa, WI (US)

(72) Inventors: Jean-Baptiste Thibault, Waukesha, WI (US); Michael J. Utschig, Wauwatosa, WI (US); Ryan J. Lemminger, New Berlin, WI (US); Sergio Lemaitre, Whitefish Bay, WI (US); Dominique Poincloux, Yvelines (FR); Uwe Wiedmann, Clifton Park, NY (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 169 days.

(21) Appl. No.: 17/658,715

(22) Filed: Apr. 11, 2022

(65) Prior Publication Data
US 2023/0320686 A1    Oct. 12, 2023

(51) Int. Cl.
A61B 6/03    (2006.01)
A61B 6/00    (2006.01)
A61B 6/40    (2024.01)

(52) U.S. Cl.
CPC ............. *A61B 6/54* (2013.01); *A61B 6/032* (2013.01); *A61B 6/4021* (2013.01); *A61B 6/56* (2013.01)

(58) Field of Classification Search
CPC .... A61B 6/00; A61B 6/03; A61B 6/54; A61B 6/4021; A61B 6/56; A61B 6/032;
(Continued)

(56) References Cited

U.S. PATENT DOCUMENTS

| 7,496,180 | B1* | 2/2009 | Subraya | ............... | H01J 35/153 |
| | | | | | 378/138 |
| 8,270,571 | B2 | 9/2012 | Bernhardt et al. | | |

(Continued)

FOREIGN PATENT DOCUMENTS

| JP | 2003331762 A | 11/2003 |
| JP | 2021083472 A | 6/2021 |
| JP | 2022046946 A | 3/2022 |
| WO | 2016136373 A1 | 9/2016 |

OTHER PUBLICATIONS

EP application 23163943.6 filed Mar. 24, 2023—partial Search Report issued Sep. 5, 2023; 11 pages.
(Continued)

*Primary Examiner* — Jurie Yun
(74) *Attorney, Agent, or Firm* — McCoy Russell LLP

(57) ABSTRACT

Methods and systems are provided for increasing a quality of computed tomography (CT) images generated by a CT system by altering a shape of a focal spot of an X-ray emitter of the CT system. In one embodiment, a method comprises controlling the CT system to focus a beam of electrons generated by a cathode of the CT system at a plurality of focal spots on a surface of an target of the CT system; generating a composite focal spot from the plurality of focal spots; and obtaining projection data of the CT system with the composite focal spot. For example, two focal spots may be combined to generate the composite focal spot. By combining focal spots to generate composite focal spots, a quality of a resulting view produced by the CT system may be increased.

20 Claims, 9 Drawing Sheets

(58) Field of Classification Search
CPC ...... H01J 35/045; H01J 35/153; H05G 1/085; H05G 1/66
See application file for complete search history.

(56) References Cited

U.S. PATENT DOCUMENTS

| | | |
|---|---|---|
| 8,401,151 B2 | 3/2013 | Frontera et al. |
| 10,980,494 B2 | 4/2021 | Lu |
| 2010/0067651 A1 | 3/2010 | Hsieh |
| 2018/0211809 A1 | 7/2018 | Burke et al. |

OTHER PUBLICATIONS

Du, Y. et al., "Non-absorption grating approach for X-ray phase contrast imaging," Optics Express, vol. 19, No. 23, Nov. 7, 2011, 6 pages.
Price, J. et al., "X-ray Source Development for X-ray Phase-Contrast Imaging," Journal on Medical Imaging, vol. 4, No. 4, Oct. 2017, 5 pages.
JP application 2023-050745 filed Mar. 28, 2023—Office Action issued May 8, 2024; Machine Translation; 4 pages.
JP2003331762 English Abstract; Espacenet search Aug. 2, 2024; 1 page.
JP2022046946 English Abstract; Espacenet search Aug. 2, 2024; 1 page.
WO2016136373 English Abstract; Espacenet search Aug. 2, 2024; 1 page.
EP application 23163943.6 filed Mar. 24, 2023—extended Search Report issued Dec. 15, 2023, 12 pages.

\* cited by examiner

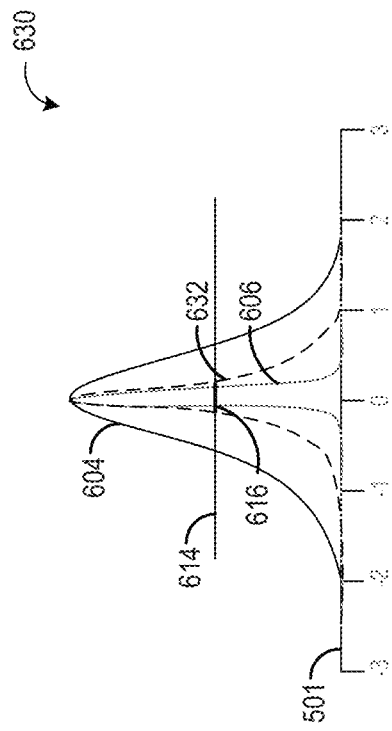
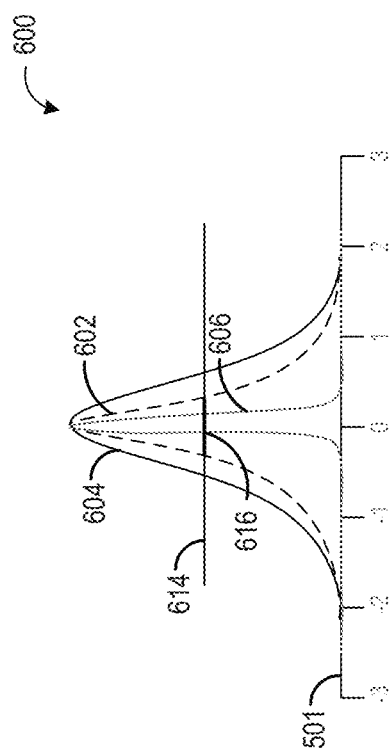
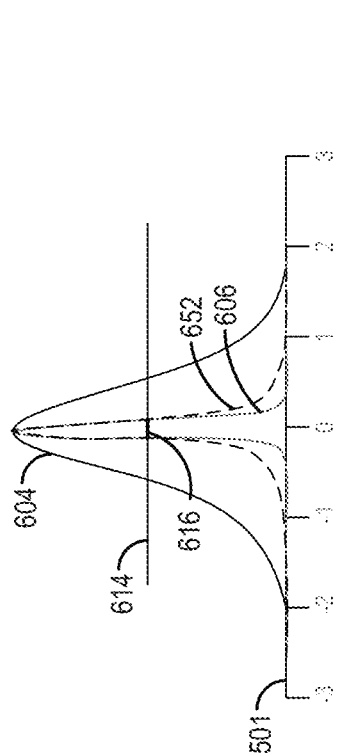

SYSTEMS AND METHODS FOR COMPUTED TOMOGRAPHY

TECHNICAL FIELD

Embodiments of the subject matter disclosed herein relate to medical imaging, and more particularly, to computerized tomography imaging systems.

BACKGROUND

In computed tomography (CT) imaging systems, an electron beam generated by a cathode is directed towards a target within an X-ray tube. In some embodiments, the target may be an anode, while in other embodiments, the X-ray tube may include an anode separate from the target. A fan-shaped or cone-shaped beam of X-rays produced by electrons colliding with the target is directed towards an object, such as a patient. After being attenuated by the object, the X-rays impinge upon an array of radiation detectors, generating an image. An area of focus in the image may depend on a focal spot of the electron beam on the target, where the focal spot is created by focusing the electron beam using focusing electrodes and/or magnets. An image generated using a larger focal spot may have a lower spatial resolution, and an image generated using a smaller focal spot may have a higher spatial resolution. Thus, to generate images with a desired area of focus and a desired spatial resolution, a CT system may be configured to generate a focal spot of a desired size and/or shape. Further, in some embodiments, the CT system may be configured to dynamically adjust a position of the focal spot from a first position to a second position in an alternating fashion between views acquired by the CT system. By alternating the position of the focal spot between consecutive views, the area of focus of the image may be increased, increasing a quality of the images.

However, the inventors herein have recognized potential issues with focal spot sizing and shaping in CT systems. In particular, the CT system may not support alternating between two or more focal spots of different sizes and/or shapes, which may combine advantages of having a smaller focal spot with advantages of having a larger focal spot. In other words, both a large area of focus and a high spatial resolution in a portion of the image may be desired, which may not be supported by current CT systems. Further, a noise distribution resulting from using different focal spots in alternating views may be reduced and a quality of the images may be increased by generating the different focal spots within a view rather than between consecutive views.

SUMMARY

The current disclosure at least partially addresses one or more of the above identified issues by a method for a computed tomography (CT) system, comprising controlling the CT system to focus a beam of electrons generated by a cathode of the CT system at a plurality of focal spots on a surface of a target of the CT system; generating a composite focal spot from the plurality of focal spots; and obtaining projection data of the CT system with the composite focal spot. For example, two focal spots may be combined to generate the composite focal spot. Combining the two focal spots may include combining various characteristics of focal spot profiles of the two focal spots, including positions, shapes, dwell times, and/or transitions of the two focal spots. By combining focal spots to generate composite focal spots, a quality of a resulting view produced by the CT system may be increased.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIG. 6A shows a first composite focal spot generated from a first focal spot and a second focal spot at a same position, based on a first dwell time, shape/size, and transition of the first focal spot and the second focal spot, in accordance with one or more embodiments of the present disclosure;

FIG. 6B shows a second composite focal spot generated from the first focal spot and the second focal spot at the same position, based on a second dwell time, shape/size, and transition of the first focal spot and the second focal spot, in accordance with one or more embodiments of the present disclosure;

FIG. 6C shows a third composite focal spot generated from the first focal spot and the second focal spot at the same position, based on a third dwell time, shape/size, and transition of the first focal spot and the second focal spot, in accordance with one or more embodiments of the present disclosure;

Figure 1:
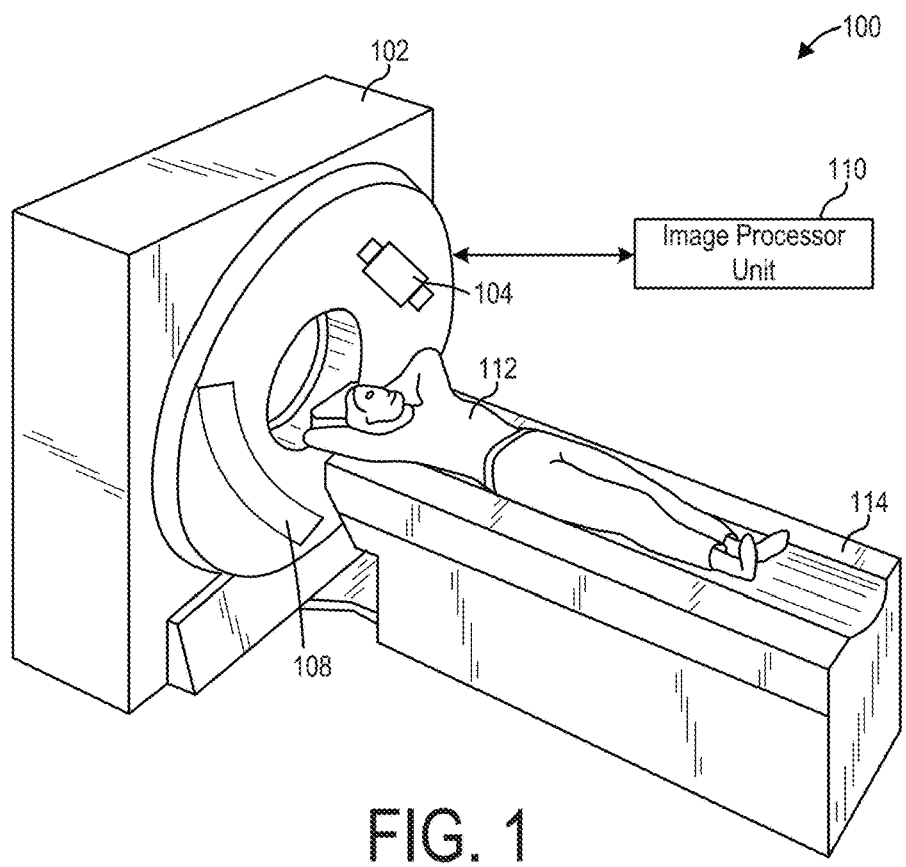
FIG. 1 shows a pictorial view of an imaging system, in accordance with one or more embodiments of the present disclosure.

The drawings illustrate specific aspects of the described systems and methods. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

This description and embodiments of the subject matter disclosed herein relate to methods and systems for a computed tomography (CT) system. Typically, in computed tomography (CT) imaging systems, an X-ray source emits a fan-shaped beam or a cone-shaped beam towards an object, such as a patient. Generally, in CT systems the X-ray source and the detector array are rotated about a gantry within an imaging plane and around the patient, and images are generated from projection data at a plurality of views at different view angles. For example, for one rotation of the X-ray source, 984 views may be generated by the CT system. The beam, after being attenuated by the patient, impinges upon an array of radiation detectors. The X-ray detector or detector array typically includes a collimator for collimating X-ray beams received at the detector, a scintillator disposed adjacent to the collimator for converting X-rays to light energy, and photodiodes for receiving the light energy from the adjacent scintillator and producing electrical signals therefrom. An intensity of the attenuated beam radiation received at the detector array is typically dependent upon the attenuation of the X-ray beam by the patient. Each detector element of a detector array produces a separate electrical signal indicative of the attenuated beam received by each detector element. The electrical signals are transmitted to a data processing system for analysis. The data processing system processes the electrical signals to facilitate generation of an image.

The X-ray source includes an X-ray tube, where a cathode emits a beam of electrons directed towards an anode of the X-ray source, striking a target of the X-ray source. A size and shape of the focal spot may partially depend on an angle of a surface of the target with respect to the beam of electrons directed towards the anode. The size and shape of the focal spot on the target may be adjusted by focusing the electron beam via electrostatic controls, electromagnetic controls, or a combination of electrostatic and electromagnetic controls. X-rays emitted as a result of the electrons colliding with the target are focused on the patient at an effective focal spot based on the focal spot.

On the target, a focal spot may have a height corresponding to a Z dimension of the patient, and a width corresponding to an X dimension of the patient. For example, the Z dimension may be aligned with a length of a body of the patient (e.g., from a head of the patient to the toes of the patient), and the X dimension may be aligned with a width of the body of the patient (e.g., from the patient's left side to the patient's right side). The height and width of the focal spot may be controlled by the electrostatic and electromagnetic controls used to focus the electron beam. Additionally, a distribution of electrons of the electron beam colliding with the target may be controlled by the electrostatic and electromagnetic controls. For example, the electrostatic and electromagnetic controls may be adjusted to generate a first focal spot with a first distribution of electrons having a first height and a first width, or the electrostatic and electromagnetic controls may be adjusted to generate a second focal spot with a second distribution of electrons having a second height and a second width, where one or more of the second distribution, second height, and second width are different from the first distribution, first height, and first width, respectively.

A quality of an image generated by the X-ray detector array may depend on a size of the focal spot. When the focal spot is larger, more X-ray flux can be delivered to the patient, which allows imaging of thicker or higher-absorbing anatomy in a shorter time. When the focal spot is smaller, less X-ray flux is delivered to the patient, when using an X-ray tube where thermal properties of the target may limit the tube current. However, when the focal spot is smaller, a spatial resolution of the image may be higher, and as the size of the focal spot increases, the spatial resolution of the image may decrease. Thus, a tradeoff may exist between power (e.g., a number of electrons colliding with the target) and spatial resolution. For some clinical tasks, higher power (e.g., a larger signal with lower spatial resolution) may be desired, while for other clinical tasks, a high spatial resolution may be desired.

A position of the focal spot on the target may also be adjusted via the electrostatic and electromagnetic controls.

In other words, the focal spot may be deflected by either or both of the electrostatic and electromagnetic controls from a first position on the target to a second position on the target. For example, the focal spot may be deflected in the X dimension, where the first position is at a first X position, and the second position is at a second X position, or the focal spot may be deflected in the Z dimension, where the first position is at a first Z position, and the second position is at a second Z position, or the focal spot may be deflected in both the X dimension and the Z dimension. Further, the CT system may provide a "2-point", "wobble" or "flying focal spot" mode, where the focal spot may alternate between the first position and the second position in consecutive views acquired by the CT system. For example, a first image of a sequence of images may be generated from a first view, where the focal spot is at the first position. A second image of the sequence may be generated from a second view, where the focal spot is at the second position. A third image of the sequence may be generated from a third view, where the focal spot is at the first position, and a fourth image of the sequence may be generated from a fourth view, where the focal spot is at the second position, and so on. By deflecting the focal spot to alternate between the first position and the second position, a quality of the images generated may be increased by increasing an overall area of focus of the images. More than 2 positions may be used, e.g. a combination of 2 positions in X and 2 positions in Z, resulting in a total of 4 different positions.

However, the mode supported by the CT system may not support alternating between two or more focal spots of different sizes and/or shapes, which may allow advantages of having a larger focal spot (e.g., greater power) with advantages of having a smaller focal spot (e.g., greater spatial resolution), as described in greater detail herein. Additionally, while the CT system may support alternating between focal spots at different positions between views, the CT system may not support generating two or more focal spots within a view. Since noise is generated each time a signal is sampled, by generating two or more focal spots within a view, an amount and/or distribution of noise in the images generated may be reduced, thereby increasing a quality of the images without increasing a dosage of radiation to which the patient is exposed.

Methods and systems are therefore proposed herein for generating a composite focal spot comprising a first focal spot of a first size and shape at the first position, and a second focal spot of a second size and shape at the second position, where the second size and shape may be different from the first size and shape. Images generated using the composite focal spot may include both a large area of focus, and a portion of the image in a high spatial resolution, thereby combining advantages of using a smaller focal spot with advantages of using a larger focal spot. A size and shape of the first focal spot and a size and shape of the second focal spot may be individually configured based on a desired profile of the composite focal spot. Further, the composite focal spot may be generated by alternating between focusing the electron beam on the first focal spot and the second focal spot within a view acquired by the CT system, or between views acquired by the CT system. A further advantage of the systems and methods described herein is that the composite focal spot may be configured using software, while relying on existing hardware configurations of X-ray tubes of the CT system.

Figure 2:
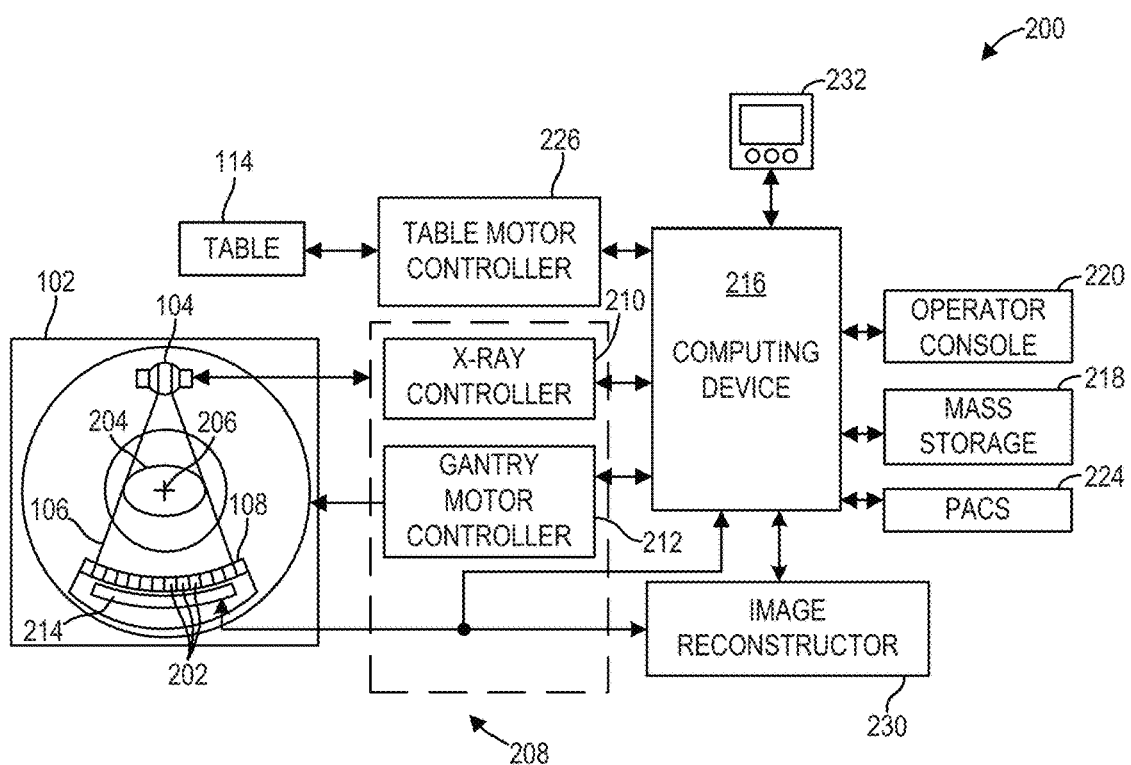
FIG. 2 shows a block schematic diagram of an exemplary imaging system, in accordance with one or more embodiments of the present disclosure.
Figures 3A, 3B:
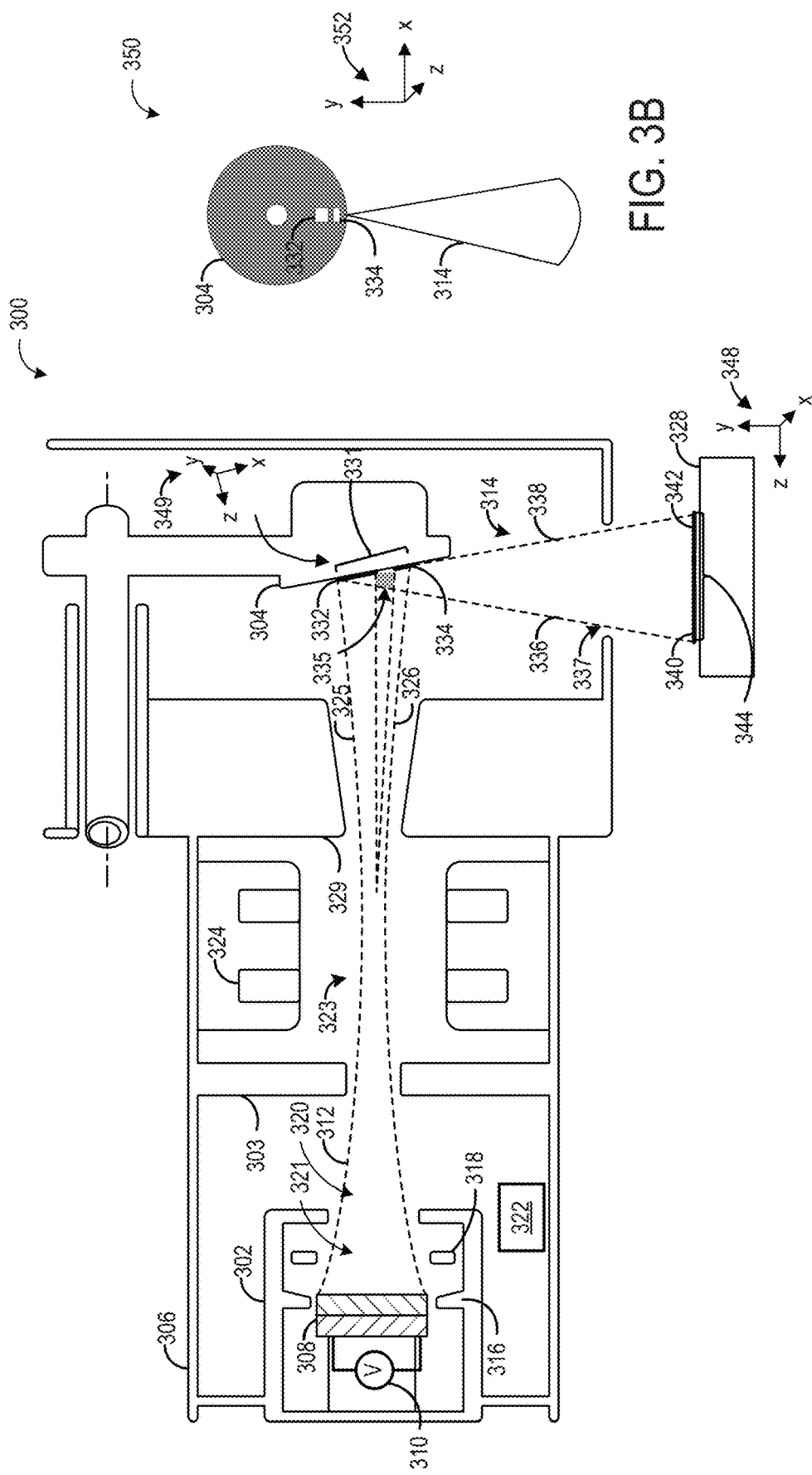
FIG. 3A is a schematic diagram of an exemplary X-ray tube, in accordance with one or more embodiments of the present disclosure.
FIG. 3B is a schematic diagram of a composite focal spot on an target, in accordance with one or more embodiments of the present disclosure.
Figure 4:
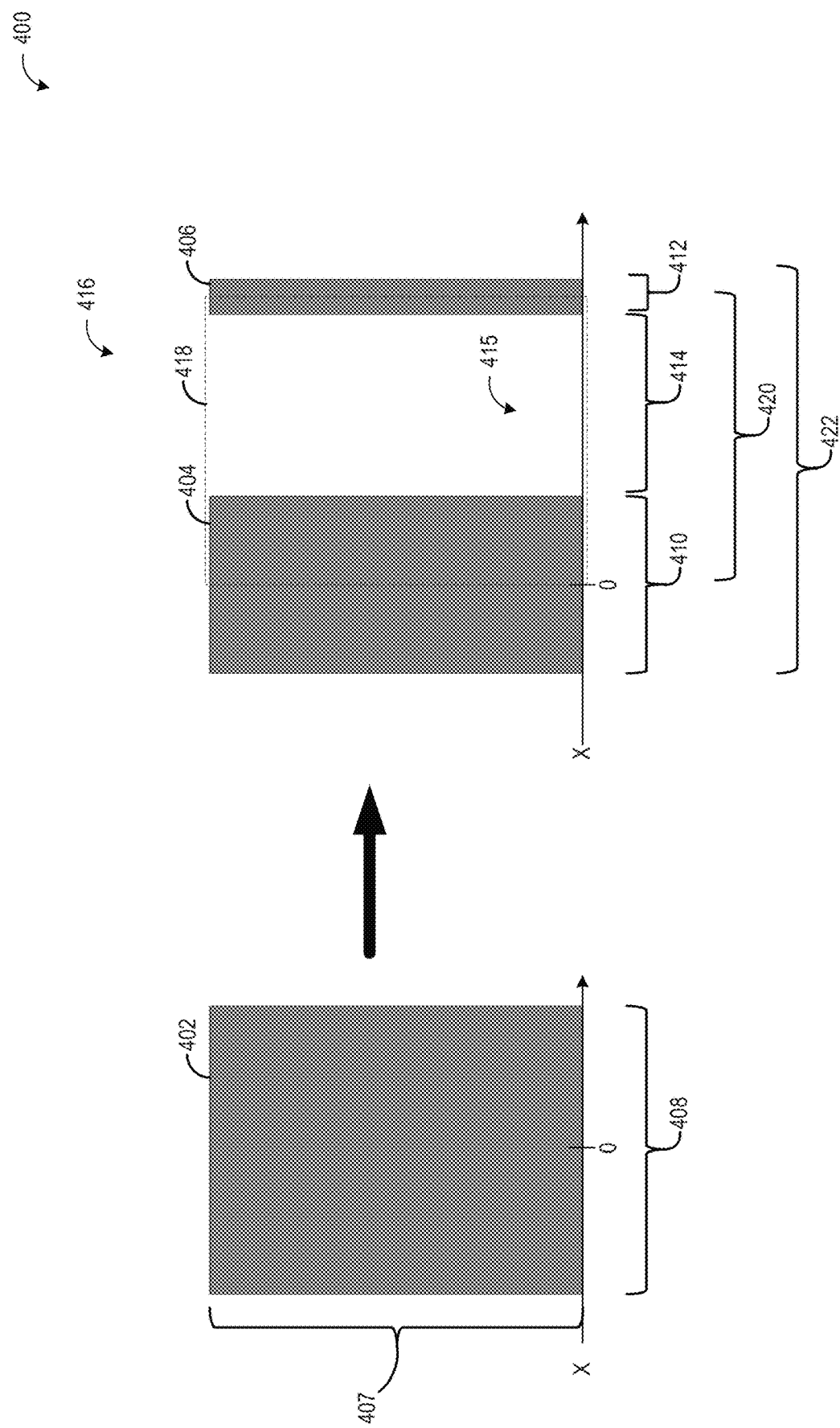
FIG. 4 shows an electron distribution diagram showing a distribution of electrons of an electron beam into a single focal spot and a composite focal spot, in accordance with one or more embodiments of the present disclosure.
Figure 5A:
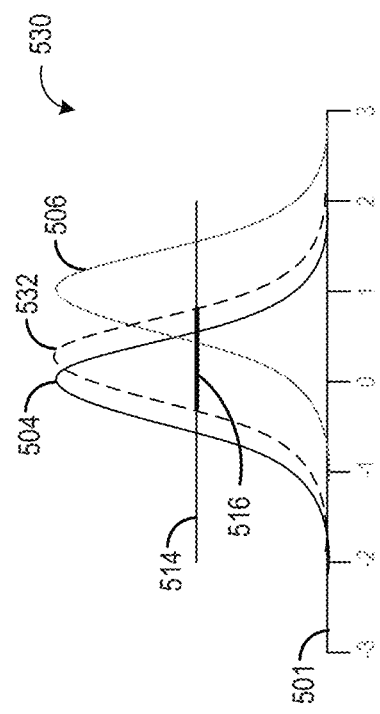
FIG. 5A shows a first composite focal spot generated from a first focal spot and a second focal spot, based on a first dwell time, position, and transition of the first focal spot and the second focal spot, in accordance with one or more embodiments of the present disclosure.
Figure 5C:
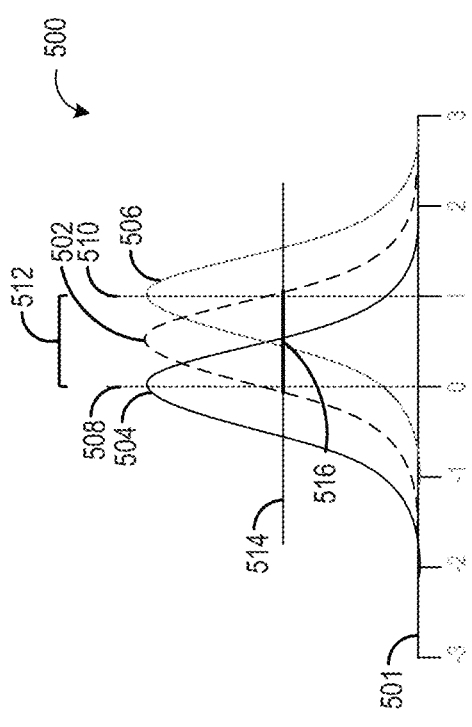
FIG. 5C shows a third composite focal spot generated from the first focal spot and the second focal spot, based on a third dwell time, position, and transition of the first focal spot and the second focal spot, in accordance with one or more embodiments of the present disclosure.
Figure 5B:
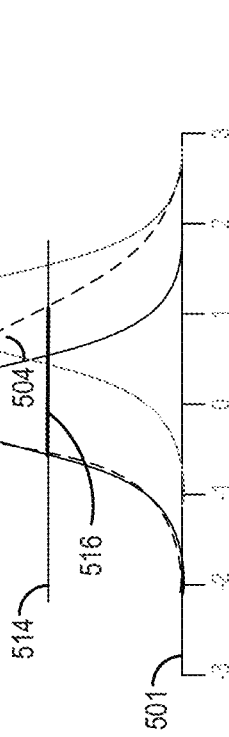
FIG. 5B shows a second composite focal spot generated from the first focal spot and the second focal spot, based on a second dwell time, position, and transition of the first focal spot and the second focal spot, in accordance with one or more embodiments of the present disclosure.
Figure 5D:
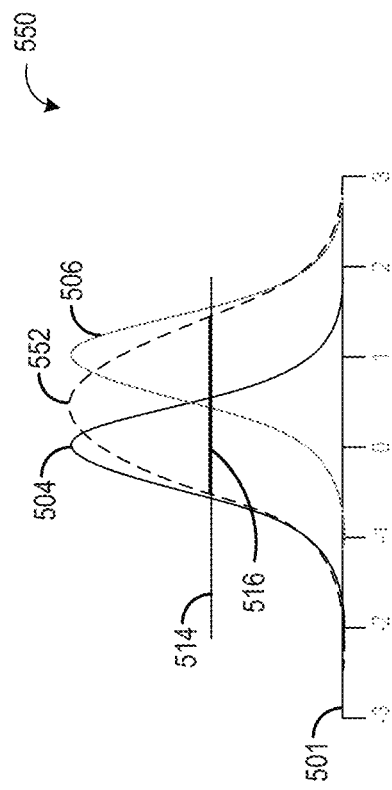
FIG. 5D shows a fourth composite focal spot generated from the first focal spot and the second focal spot, based on a fourth dwell time, position, and transition of the first focal spot and the second focal spot, in accordance with one or more embodiments of the present disclosure.
Figure 7A:
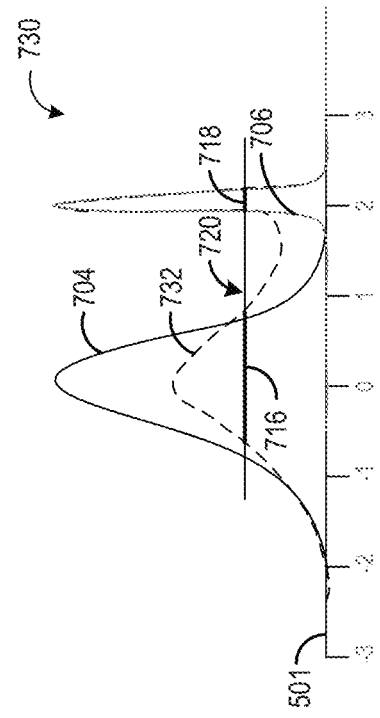
FIG. 7A shows a first composite focal spot generated from a first focal spot of a first size and shape at a first position and a second focal spot of a second size and shape at a second position, based on a first dwell time and transition of the first focal spot and the second focal spot, in accordance with one or more embodiments of the present disclosure.
Figure 7B:
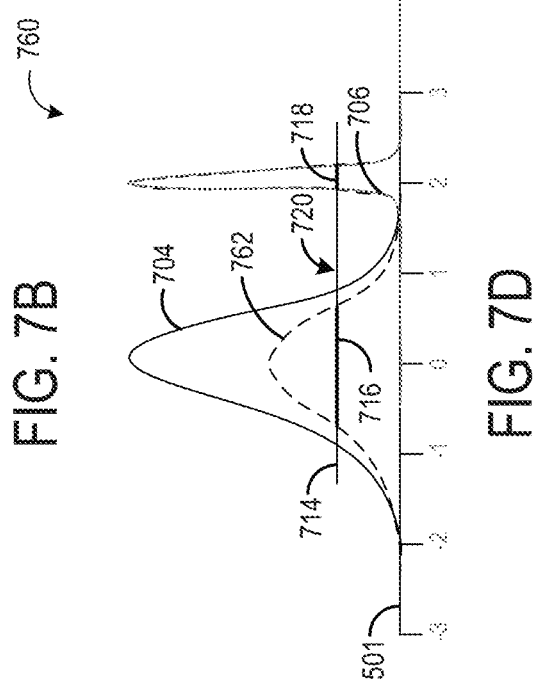
FIG. 7B shows a second composite focal spot generated from the first focal spot and the second focal spot of FIG. 7A, based on a second dwell time and transition of the first focal spot and the second focal spot, in accordance with one or more embodiments of the present disclosure.
Figure 7C:
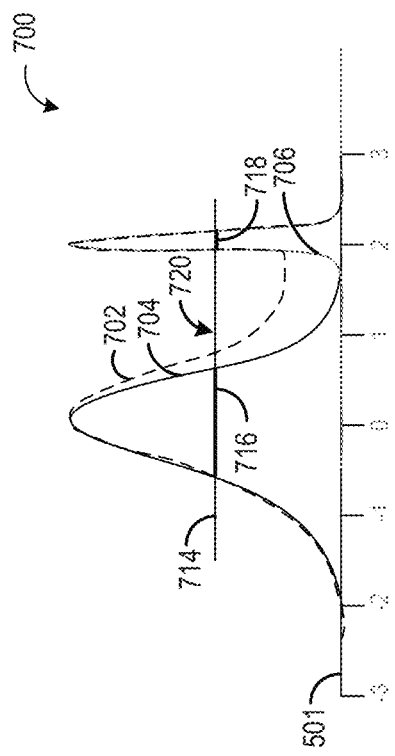
FIG. 7C shows a third composite focal spot generated from the first focal spot and the second focal spot of FIG. 7A, based on a third dwell time and transition of the first focal spot and the second focal spot, in accordance with one or more embodiments of the present disclosure.
Figure 7D:
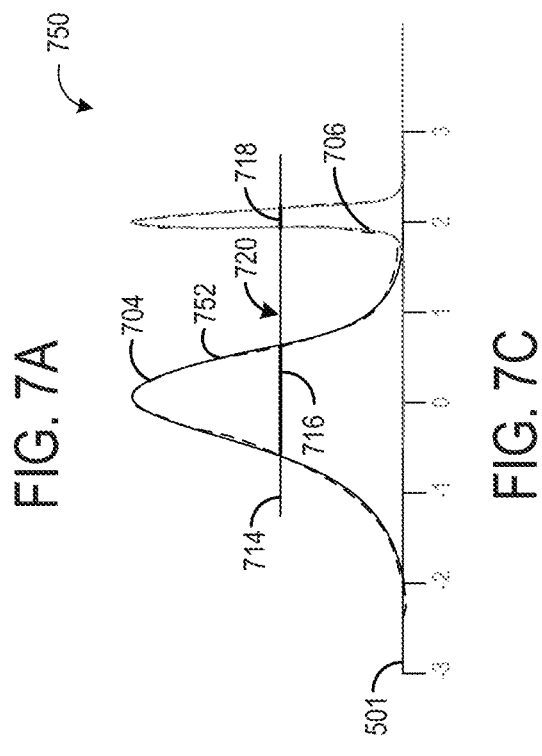
FIG. 7D shows a fourth composite focal spot generated from the first focal spot and the second focal spot of FIG. 7A, based on a fourth dwell time and transition of the first focal spot and the second focal spot, in accordance with one or more embodiments of the present disclosure.
Figure 7E:
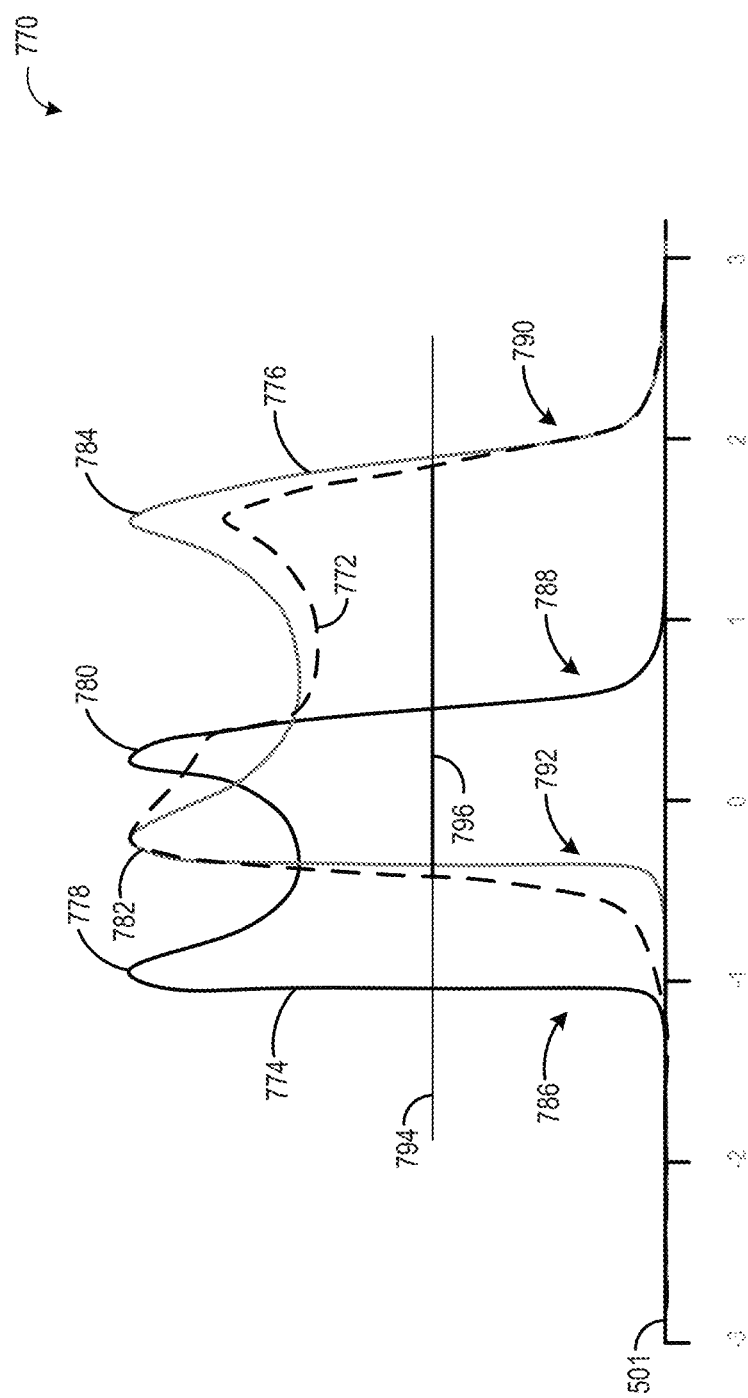
FIG. 7E shows a fifth composite focal spot generated from a first focal spot of a first size and shape at a first position and a second focal spot of a second size and shape at a second position, based on a dwell time and transition of the first focal spot and the second focal spot, in accordance with one or more embodiments of the present disclosure.

An example of a CT system that may be used to perform contrast scans in accordance with the present techniques is provided in FIGS. 1 and 2. FIG. 3A shows an example X-ray tube, where an electron beam is focused on a target at a composite focal spot, such as the composite focal spot shown in FIG. 3B. FIG. 4 illustrates how a composite focal spot comprising two discrete focal spots may be generated, where an overall size of the composite focal spot may be increased without increasing a power of the electron beam. The two discrete focal spots may be depicted as distributions of electrons striking a target of the X-ray tube, as shown in FIGS. 5A-8. FIGS. 5A-7E show various electron distributions of different sizes, shapes, and positions, corresponding to various composite focal spots. FIG. 5A shows a first composite focal spot generated from a first focal spot and a second focal spot of a same size, based on a first dwell time, position, and transition of the first focal spot and the second focal spot. FIG. 5B shows a second composite focal spot generated from the first focal spot and the second focal spot of FIG. 5A, based on a second dwell time, position, and transition of the first focal spot and the second focal spot. FIG. 5C shows a third composite focal spot generated from the first focal spot and the second focal spot of FIG. 5A, based on a third dwell time, position, and transition of the first focal spot and the second focal spot. FIG. 5D shows a fourth composite focal spot generated from the first focal spot and the second focal spot of FIG. 5A, based on a fourth dwell time, position, and transition of the first focal spot and the second focal spot. FIG. 6A shows a first composite focal spot generated from a first focal spot and a second focal spot at a same position, based on a first dwell time, shape/size, and transition of the first focal spot and the second focal spot. FIG. 6B shows a second composite focal spot generated from the first focal spot and the second focal spot of FIG. 6A, based on a second dwell time, shape/size, and transition of the first focal spot and the second focal spot. FIG. 6C shows a third composite focal spot generated from the first focal spot and the second focal spot of FIG. 6A, based on a third dwell time, shape/size, and transition of the first focal spot and the second focal spot. FIG. 7A shows a first composite focal spot generated from a first focal spot of a first size and shape at a first position and a second focal spot of a second size and shape at a second position, based on a first dwell time and transition of the first focal spot and the second focal spot. FIG. 7B shows a second composite focal spot generated from the first focal spot and the second focal spot of FIG. 7A, based on a second dwell time and transition of the first focal spot and the second focal spot. FIG. 7C shows a third composite focal spot generated from the first focal spot and the second focal spot of FIG. 7A, based on a third dwell time and transition of the first focal spot and the second focal spot. FIG. 7D shows a fourth composite focal spot generated from the first focal spot and the second focal spot of FIG. 7A, based on a fourth dwell time and transition of the first focal spot and the second focal spot. FIG. 7E shows a fifth composite focal spot generated from a first focal spot of a first size and shape at a first position and a second focal spot of a second size and shape at a second position, based on a dwell time and transition of the first focal spot and the second focal spot. The fifth composite focal spot of FIG. 7E may include side lobes, such as the side lobes depicted in FIG. 8. The composite focal spot may be generated by following one or more steps of a method described in reference to FIG. 9.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one X-ray source 104 configured to project a beam of X-ray radiation 106 (see FIG. 2) for use in imaging the subject 112 laying on a table 114. Specifically, the X-ray source 104 is configured to project the X-ray radiation beams 106 towards a detector array 108 positioned on the opposite side of the gantry 102. Although FIG. 1 depicts a single X-ray source 104, in certain embodiments, multiple X-ray sources and detectors may be employed to project a plurality of X-ray radiation beams for acquiring projection data at different energy levels corresponding to the patient. In some embodiments, the X-ray source 104 may enable dual-energy gemstone spectral imaging (GSI) by rapid peak kilovoltage (kVp) switching. In some embodiments, the X-ray detector employed is a photon-counting detector which is capable of differentiating X-ray photons of different energies. In other embodiments, two sets of X-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an X-ray source projects a cone-shaped X-ray radiation beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of an X-ray radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray source and the detector array are rotated with a gantry within the imaging plane and around the object to be imaged such that an angle at which the X-ray beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector.

The X-ray source 104 includes an anode and a cathode. Electrons emitted by the cathode (e.g., resulting from energization of the cathode) may be intercepted by a target arranged at or near the anode. Electrons intercepted by the target may release energy in the form of X-rays, with the X-rays being directed toward the detector array 108. An area of the target surface that receives the electrons from the cathode and forms the emitted X-rays may be referred to herein as a "focal spot." The emitted X-rays may be focused on a portion of the scanned subject 204, at an "effective focal spot". A size of the effective focal spot may depend on an angle of the actual focal spot (e.g., on the target surface). For example, a small effective focal spot may be desirable when scanning a small area, while a large effective focal spot may be desirable when scanning a larger area.

In some embodiments, an X-ray generation system including the X-ray source 104 may move and/or shape the focal spot. For example, the X-ray generation system may increase or decrease a size of the focal spot. Additionally, in some embodiments, the X-ray generation system may generate a composite focal spot, where the composite focal spot is combination of two or more discreet focal spots. For example, two discreet focal spots located apart from each other may be combined to produce a single, composite focal spot. Composite focal spots are described in greater detail below in reference to FIGS. 3-9.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the X-ray radiation beam 106 (see FIG. 2) that pass through the subject 204 (such as a patient) to acquire corresponding projection data. In some embodiments, the detector array 108 may be fabricated in a multi-slice configuration including the plurality of rows of cells or detector elements 202, where one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections. In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a 3D volumetric image of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may be any type of non-transitory memory and may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Referring now to FIG. 3A, an exemplary X-ray tube 300 is shown. In one embodiment, the X-ray tube 300 may be the X-ray source 104 (see FIGS. 1-2). In the illustrated embodiment, the X-ray tube 300 includes an exemplary cathode 302 and an anode 303 disposed within a tube casing 306. The cathode may include one or more emitters 308. The one or more emitters 308 may be flat emitters, or curved emitters that are concave in curvature, providing pre-focusing of the electron beam. In other embodiments, a shaped emitter such as a square, rectangular, elliptical, or circular emitter may be employed. It may be noted that emitters of different shapes or sizes may be employed based on the application requirements. For example, in some embodiments, two emitters 308 may used, where a first emitter 308 may generate a first focal spot on the target 304, and a second emitter 308 may generate a second focal spot on the target 304, as described in greater detail below.

In the present example, the cathode 302, and in particular the one or more emitters 308, may be directly heated by passing a current through the one or more emitters 308, which may be supplied by a voltage source 310. In one embodiment, a current of about 10 amps (A) may be passed through the one or more emitters 308. The one or more emitters 308 may emit an electron beam 312 as a result of being heated by the current supplied by the voltage source 310. As used herein, the term "electron beam" may be used to refer to a stream of electrons that have substantially similar velocities.

The electron beam 312 may be directed towards a target 304 to produce X-rays 314. More particularly, the electron beam 312 may be accelerated from the emitter 308 towards the target 304 by applying a potential difference between the one or more emitters 308 and the anode 303. In one embodiment, a high voltage in a range from about 40 kV to about 450 kV may be applied to set up the potential difference between the one or more emitters 308 and the anode 303, thereby generating one or more electric fields 320 in the X-ray tube 300. In one embodiment, a high voltage differential of about 140 kV may be applied between the one or more emitters 308 and the anode 303 to accelerate the electrons in the electron beam 312 towards the target 304. As an example, the one or more emitters 308 may be at a potential of about −140 kV and the anode 303 and target 304 may be at ground potential or about zero volts.

When the electron beam 312 impinges upon the target 304, heat may be generated in the target 304, which may be significant enough to melt the target 304. In various embodiments, a rotating target may be used to circumvent the problem of heat generation in the target 304. For example, the target 304 may be configured to rotate such that the electron beam 312 striking the target 304 does not strike the target 304 at the same location, whereby the target 304 may not melt. In various embodiments, the target 304 may include materials such as, but not limited to, tungsten or molybdenum. A size of a focal spot on the target 304 may also be adjusted to reduce an amount of heat generated in the target 304, where a smaller focal spot may generate a greater amount of heat at a specific location. An electron collector 329, held at a same potential as the target 304, serves as a sink of electrons that bounce off the surface of 304 during the initial impact, which reduces the chance of those same electrons re-striking the target. Collecting the backscattered electrons in this way further reduces target heating.

The X-ray tube 300 may include one or more focusing electrodes 316, which may be disposed adjacent to the emitter 308 such that the one or more focusing electrodes 316 focus the electron beam 312 towards the target 304. As used herein, the term "adjacent" means near to in space or position. To focus the electron beam 312, voltages may be applied to the one or more focusing electrodes 316 to generate the one or more electric fields 321. The voltages may be different for each of the one or more focusing electrodes 316. For example, a first voltage may be applied to a first focusing electrode 316; a second voltage may be applied to a second focusing electrode 316; a third voltage may be applied to a third focusing electrode 316; and so on. For some focusing electrodes 316, the voltage may be 0, where no voltage is applied to the focusing electrode 316. In some embodiments, a first portion of the focusing electrodes 316 may be used for deflecting the electron beam 312, and a second portion of the focusing electrodes 316 may be used for focusing the electron beam 312. In this way, the voltages may be selectively applied by a controller of a control electronics module 322 to generate one or more specific electric fields that focus the electron beam 312 to a desired shape and deflect the electron beam 312 to a desired position.

In some embodiments, the one or more focusing electrodes 316 may each be maintained at a voltage potential that is less than a voltage potential of the one or more emitters 308. The potential difference between the one or more emitters 308 and the one or more focusing electrodes 316 may prevent electrons generated from the one or more emitters 308 from moving towards the one or more focusing electrodes 316. In some embodiments, the one or more focusing electrodes 316 may be maintained at a negative potential with respect to that of the one or more emitters 308. The negative potential of the one or more focusing electrodes 316 with respect to the one or more emitters 308 may focus the electron beam 312 away from the one or more focusing electrodes 316, thereby facilitating focusing of the electron beam 312 towards the target 304.

In other embodiments, the one or more focusing electrodes 316 may be maintained at a voltage potential that is equal to or substantially similar to the voltage potential of the one or more emitters 308. The similar voltage potential of the one or more focusing electrodes 316 with respect to the voltage potential of the one or more emitters 308 may create a parallel electron beam by shaping electrostatic fields due to the shape of the one or more focusing electrodes 316. The one or more focusing electrodes 316 may be maintained at a voltage potential that is equal to or substantially similar to the voltage potential of the one or more emitters 308 via use of a lead coupling the emitter 308 and the one or more focusing electrodes 316.

Additionally, the X-ray tube 300 may include one or more extraction electrodes 318, which may be used for additionally controlling and focusing the electron beam 312 towards the anode 303. The one or more extraction electrodes 318 may be located between the anode 303 and the one or more emitters 308. In some embodiments, the one or more extraction electrodes 318 may be positively biased by supplying a desired voltage to the one or more extraction electrodes 318.

An energy of the electron beam 312 may be controlled in various ways. For instance, the energy the electron beam 312 may be controlled by altering the potential difference (e.g., an acceleration voltage) between the cathode 302 and the anode 303. As used herein, the term "electron beam current" refers to a flow of electrons per second between the cathode 302 and the anode 303. The current of the electron beam 312 may be controlled by adjusting the emitter voltage 310 to change the temperature of the emitter 308. The electron beam current may be controlled by altering the voltage applied to the one or more extraction electrodes 318. It may be noted that the one or more emitters 308 may be treated as an infinite source of electrons.

The one or more electric fields 321 may be generated between the one or more extraction electrodes 318 and the one or more focusing electrodes 316 due to a potential difference between the one or more focusing electrodes 316 and the one or more extraction electrodes 318. A strength of the one or more electric fields 320 may be employed to control the intensity of electron beam 312 generated by the one or more emitters 308 towards the anode 303. More particularly, the one or more electric fields 320 may cause the electrons emitted by the one or more emitters 308 to be accelerated towards the anode 303. The stronger the one or more electric fields 320, the stronger the acceleration of the electrons from the one or more emitters 308 towards the anode 303. Alternatively, the weaker the one or more electric fields 320, the lesser the acceleration of electrons from the one or more emitters 308 towards the anode 303. The intensity of the electron beam 312 striking the target 304 may thus be controlled by the one or more electric fields 320 and 321.

Furthermore, voltage shifts of 8 kV or less may be applied to the one or more extraction electrodes 318 to control the intensity of the electron beam 312. In certain embodiments, these voltage shifts may be applied to the one or more extraction electrodes 318 via use of the control electronics module 322. The control electronics module 322 may be a non-limiting embodiment of, or may be a part of X-ray controller 210 of FIG. 2.

In some embodiments, a composite focal spot may be generated as a result of electrostatic focusing, by selectively applying the voltages to the focusing electrodes 316. As the electron beam 312 is focused on the target 304, the electrons may form a Gaussian distribution. For the purposes of this disclosure, the Gaussian distribution may be an approximately Gaussian distribution.

The Gaussian distribution of electrons of the electron beam 312 may be narrowed or parallelized, where electrons colliding with the target 304 at sides of the Gaussian distribution may be directed towards a center of the Gaussian distribution. Said a different way, a distribution of electrons at the sides of the Gaussian distribution may be inverted. As a result of the narrowing or parallelizing of the Gaussian distribution, an intensity of the electron beam 312 may be greater at the sides (e.g., outer edges) of the Gaussian distribution than an intensity of the electron beam 312 at the center of the Gaussian distribution. When the intensity of the electron beam 312 is greater at the sides of the Gaussian distribution than at the center, this may be visually depicted in a plot of the Gaussian distribution as "side lobes" formed at edges of the plot. The voltages may be applied to the focusing electrodes 316 to generate side lobes at both sides of the Gaussian distribution (e.g., in a dimension, such as an X dimension or a Y dimension as indicated by the coordinate axes 349 and 352), or the voltages may be applied to the focusing electrodes 316 to generate a side lobe at one side of the Gaussian distribution.

When the electrons of the Gaussian distribution with side lobes collide with the target 304 to generate a focal spot, portions of the focal spot corresponding to the side lobes may receive a greater number of electron collisions than central portions of the focal spot, generating the composite focal spot. As a result, images generated using the composite focal spot created by electrostatic focusing may include a large area of focus (e.g., corresponding to an overall size of the composite focal spot), and a smaller area with high spatial resolution within the large area of focus (e.g. corresponding to the side lobes). Thus, by controlling the voltages applied to the focusing electrodes 316, a shape and size of the composite focal spot, including a shape and size of a first component focal spot (e.g., corresponding to the overall distribution of electrons) and additional component focal spots (e.g., corresponding to electron distributions of the side lobes). Generation of composite focal spots including component focal spots with side lobes is described in greater detail below in reference to FIG. 7E.

Additionally, the X-ray tube 300 may also include a one or more magnets 324 for focusing and/or positioning and deflecting the electron beam 312 onto the target 304. In various embodiments, the one or more magnets 324 may be disposed between the cathode 302 and the target 304. In some embodiments, the one or more magnets 324 may include one or more multipole magnets for influencing focusing of the electron beam 312 by creating one or more magnetic fields 323 that shapes the electron beam 312 on the target 304. The one or more multipole magnets may include one or more quadrupole magnets, one or more dipole magnets, or combinations thereof. For example, dipole magnets may be used to deflect the electron beam 312, positioning the electron beam 312 in a first dimension, while quadrupole magnets may be used to focus the electron beam 312 in two dimensions (e.g., a length and a width of the electron beam 312). For example, in a first step, the electron beam generated by the one or more emitters 308 may be deflected and focused by electrostatic focusing. In a second step, the electron beam may be further deflected by the one or more dipole magnets, to adjust a position of a focal spot of the electron beam on the target 304. In a third step, which may occur before or after the second step, the electron beam may be focused to generate a desired distribution of electrons on the target (e.g., a desired shape of the focal spot).

As properties of the electron beam current and voltage change, electrostatic focusing of the electron beam 312 will change accordingly. In order to maintain a stable size, shape, and other characteristics of a focal spot, or quickly modify focal spot size and/or shape according to system requirements, the one or more magnets 324 may provide a magnetic field having a performance controllable from steady-state to a sub-30 microsecond time scale for a wide range of focal spot sizes and shapes. When the electron beam 312 has been focused and positioned, the electron beam 312 impinges upon the target 304 to generate the X-rays 314. The X-rays 314 generated by collision of the electron beam 312 with the target 304 may be directed from the X-ray tube 300 through an opening in the tube casing 306, at an X-ray window 337, towards an object 328.

As described in greater detail in FIGS. 4-8, in various embodiments, the electron beam 312 may be electrostatically and/or magnetically controlled and focused to generate a composite focal spot comprising two distinct focal spots. More specifically, the electron beam 312 may be electrostatically and/or magnetically controlled and focused to alternate between a first electron beam 325 and a second electron beam 326, which generate a composite focal spot 331 comprising a first focal spot 332 and a second focal spot 334, respectively, on the target 304. In other words, the first electron beam 325 may generate the first focal spot 332 and the second electron beam 326 may generate the second focal spot 334. The first focal spot 332 and the second focal spot 334 may be separated by a space 335, representing a portion of the target 304 where a number of electrons of the first electron beam 325 and the second electron beam 326 colliding with the target 304 is minimized. In other words, electrons of the first electron beam 325 may impinge on the target at a location of the first focal spot 332 with a first distribution, electrons of the second electron beam 326 may impinge on the target at a location of the second focal spot 334 with a second distribution, and at an intersection of the first distribution and the second distribution at the location of the space 335, a smaller number of electrons may impinge on the target 304.

Further, in some embodiments, the first electron beam 325 may be focused on the target 304 for a first duration, and the second electron beam 326 may be focused on the target 304 for a second duration, and no electron beam may be focused on the target 304 for a third duration between the first duration and the second duration. In other words, during a transition from the first electron beam 325 to the second electron beam 326, the electron beam from one or more emitters 308 may be inhibited or "gridded" by electrode 318 whereby no electron beam is generated. In some embodiments, the one or more emitters 308 may be gridded in response to a duration of the transition exceeding a threshold transition time. In other words, if a transition time is fast (e.g., less than the threshold transition time), the one or more emitters 308 may not be gridded, and if the transition time is slow (e.g., greater than the threshold transition time), the one or more emitters 308 may be gridded.

As a result of no electron beam being generated during the transition, a number of electrons colliding with the target 304 at the space 335 may be minimized. Switching off the one or more emitters 308 between the first duration and the second duration may be referred to as beam blanking or blanking. A result of blanking may be that a power of the first electron beam 325 and the second electron beam 326 may be maximized (e.g., by minimizing electron collisions on the target 304 between the first focal spot and the second focal spot).

As a result of the first electron beam portion 325 colliding with target 304 at the first focal spot 332, a first set of X-rays 336 may be generated and directed out X-ray window 337 towards the object 328. The first set of X-rays 336 may intersect with the object 328 at a first effective focal spot 340. As a result of the second electron beam portion 326 colliding with target 304 at the second focal spot 334, a second set of X-rays 338 may be generated and directed out X-ray window 337 towards the object 328. The second set of X-rays 338 may intersect with the object 328 at a second effective focal spot 342, which may overlap with the first effective focal spot 340. Thus, the first set of X-rays 336 and the second set of X-rays 338 generated from the composite focal spot 331 may be focused at a composite effective focal spot 344 on the object 328. The composite effective focal spot may have a width (in an X dimension, as indicated by coordinate axes 348) and a length (in an Z dimension, as indicated by the coordinate axes 348).

A size of the first focal spot 332 may be different than a size of the second focal spot 334. For example, the first focal spot 332 may be larger than the second focal spot 334, or the first focal spot 332 may be smaller than the second focal spot 334. Additionally a shape of the first focal spot 332 may be different than a shape of the second focal spot 334. For example, the first focal spot 332 may have a first shape with a first width (in an X dimension, as indicated by coordinate axes 349) and a first height (in an Y dimension, as indicated by the coordinate axes 349), and the second focal spot 334 may have a second shape with a second width and a second height, where the first height and the first width may be different from the second height and the second width, respectively. A size and shape of the space 335 may also vary. For example, a distance between the first focal spot 332 and the second focal spot 334 (e.g., the spacing 335) may be large, or the distance between the first focal spot 332 and the second focal spot 334 may be small.

For example, FIG. 3B shows a front view of the target 304, including the first focal spot 332 and the second focal spot 334. In FIG. 3B, the first focal spot 332 is depicted as having a similar width as the second focal spot 334 (in an X dimension, as indicated by coordinate axes 352), but a larger height than second focal spot 334 (in a Y dimension, as indicated by coordinate axes 352). The first focal spot 332 is also depicted as having a square shape, while the second focal spot 334 is depicted as having a rectangular shape. The space 335 between the first focal spot 332 and the second focal spot 334 has a width equal to the first focal spot 332 and the second focal spot 334, and a height that is less than the height of the first focal spot 332 and the second focal spot 334. As described above, the target 304 may be a circular target that rotates such that the first focal spot 332 and the second focal spot 334 are generated at different locations on a surface of the target 304 as the target 304 rotates. By generating the first focal spot 332 and the second focal spot 334 at different locations on the surface of the target 304, an amount of heat absorbed at a location of the target 304 may be minimized.

Referring now to FIG. 4, an electron distribution diagram 400 shows an initial distribution of electrons of an electron beam of a CT system into a single focal spot 402, which as a result of electrostatic and/or magnetic focusing, may be split into a composite focal spot 416 comprising a first distribution of electrons into a first focal spot 404 and a second distribution of electrons into a second focal spot 406. The composite focal spot 416 may be the same as or similar to the composite focal spot 331 of FIG. 3A. In other words, the single focal spot 402 may be generated by the electron beam 312, and the first focal spot 404 may be the same as or similar to the first focal spot 332 of FIG. 3A generated by focusing the first electron beam 325 on the target 304, and the second focal spot 406 may be the same as or similar to the second focal spot 334 of FIG. 3A generated by focusing the second electron beam 326 on the target 304.

A size and shape of the single focal spot 402 may depend on one or more electric fields (e.g., the one or more electric fields 321) generated by one or more focusing electrodes (e.g., the one or more focusing electrodes 316) and one or more magnetic fields (e.g., the magnetic fields 323) generated by one or more magnets (e.g., the one or more magnets 324). For example, the one or more electric fields may perform a first focusing of an electron beam (e.g., electron beam 312, 325, or 326) to generate an initial focal spot of a first size and shape, and deflect the electron beam to a desired position on a target of the CT system; the first size and shape of the initial focal spot may be further refined to a second size and shape by magnetic fields of quadrupole magnets of the one or more magnets; and the resulting focal spot may be further deflected by dipole magnets of the one or more magnets to adjust the position of the focal spot to the desired position.

The distributions of electrons generating the focal spots of FIG. 4 (e.g., the single focal spot 402, the first focal spot 404, and the second focal spot 406) are depicted as having a shape that is rectangular. While the rectangular shape may be approximated on the target as a result of a configuration of the one or more electric fields, the one or more magnetic fields, and various shields or barriers of the CT system, it should be appreciated that the distribution of electrons throughout the focal spots may not be uniform, but rather based on combinations of Gaussian distributions generated by the configuration of the one or more electric fields and/or the one or more magnetic fields. Different possible shapes of the Gaussian distributions are described further below in reference to FIGS. 5A-8.

The single focal spot 402 may have a length 407 and a width 408, as measured along an X-axis of the first focal spot 402. Thus, the single focal spot 402 may have a first size based on the height 407 and the width 408. When taken together or combined, the first focal spot 404 and the second focal spot 406 may have a size equivalent to the first size of the single focal spot 402. In other words, the first focal spot 404 and the second focal spot 406 may have the same length 407 as the single focal spot 402. The first focal spot 404 may have a width 410, and the second focal spot 406 may have a width 412, where a sum of the width 410 and the width 412 may equal the width 408. Thus, a total area occupied by the first focal spot 404 and the second focal spot 406 may be equivalent to a total area occupied by the single focal spot 402.

The first focal spot 404 and the second focal spot 406 of the composite focal spot 416 may be separated by a space 415 (e.g., the space 335 of FIG. 3A). The space 415 may have a width 414, which may vary depending on a desired size of the composite focal spot 416. If the size of the composite focal spot 416 is desired to be larger, the width 414 of the space 415 may be increased. If the size of the composite focal spot 416 is desired to be smaller, the width 414 of the space 415 may be decreased. Thus, by separating the first focal spot 404 and the second focal spot 406 by the space 415, a size of the composite focal spot 416 may be increased to a size greater than the size of the single focal spot 402, indicated within composite focal spot 416 by a dashed rectangle 418. In other words, a width 420 of the dashed rectangle 418 may be equivalent to the width 408 of single focal spot 402, which may be less than a total with 422 of the composite focal spot 416.

For example, a CT system may have a capacity to generate a single focal spot with a maximum width of 2.5 mm, whereby the width 408 of the first focal spot 402 may be 2.5 mm. For imaging a specific anatomical structure of a patient, a focal spot with a larger width of 4.5 mm may be desired. To generate a focal spot with the larger width of 4.5 mm, the composite focal spot 416 may be created, where the single focal spot 402 may be divided into two focal spots, meaning, the first focal spot 404 and the second focal spot 406. In an embodiment, the width 410 of the first focal spot 404 may be 2.0 mm, corresponding to 80% of the width 408 of the single focal spot 402, and the width 412 of the third focal spot 404 may be 0.5 mm, corresponding to 20% of the width 408 of the single focal spot 402. The width 408 (2.5 mm) of the single focal spot 402 may be the sum of the width 410 (2.0 mm) of the first focal spot 404 and the width 412 (0.5 mm) of the second focal spot 406. The first focal spot 404 may then be separated from the second focal spot 406 by 2.25 mm (e.g., the width 414), such that the width 422 of the composite focal spot 416 is the desired width of 4.5 mm, which is greater than the width 420 (2.5 mm).

The composite focal spot 416 may be generated in various ways. In some embodiments, the composite focal spot 416 may be generated by controlling an activation of one or more emitters (e.g., the one or more emitters 308) and a generation of the electrostatic and/or magnetic fields. For example, a single emitter of the one or more emitters may be activated with a first, lower power to generate the first focal spot 404, and the single emitter may be activated with a second, higher power to generate the second focal spot 406. As the single emitter is activated with the first, lower power, an amount of energy delivered to the one or more focusing electrodes and an amount of energy (e.g., current) delivered to the one or more magnets may be controlled to focus the electron beam on the target at the first focal spot 404. As the single emitter is activated with the second, higher power, the amount of energy delivered to the one or more focusing electrodes and the amount of energy delivered to the one or more magnets may be controlled to focus the electron beam on the target at the second focal spot 406. A method for activating an emitter of a cathode to generate two or more focal spots is described in FIG. 9.

Alternatively, in various embodiments, two or more different emitters may be used to generate the first focal spot 404 and the second focal spot 406. For example, a first electron beam (e.g., the electron beam 325) may be generated by a first emitter (e.g., of the one or more emitters 308 of FIG. 3A), and a second electron beam (e.g., the electron beam 326) may be generated by a second emitter. The first emitter may generate the first focal spot 404 and the second electron beam may generate the second focal spot 406. In some embodiments, the first emitter and the second emitter may be configured to activate concurrently, such that the first focal spot 404 and the second focal spot 406 are generated concurrently on a target (e.g., the target 304). For example, the first emitter and the second emitter may be separated by a first distance, and the one or more electric fields and the one or more magnetic fields may generate the first focal spot 404 and the second focal spot 406 separated by a second distance, where the second distance is based on the first distance.

An emitter (e.g., the first emitter and/or the second emitter) may include a filament with a coil diameter. An amount of power generated by the emitter may depend on the coil diameter. For example, if the coil diameter is larger, a greater amount of power (e.g. a greater number of electrons) may be generated by the emitter. If the coil diameter is smaller, less power may be generated by the emitter. Additionally, shape of a focal spot (e.g., the first focal spot 404 and/or the second focal spot 406) may be based on a shape of the emitter. For example, the emitter may be flat, which may generate a first electron distribution, or the emitter may be curved, which may generate a second, different electron distribution. As a result of the different emitter shapes, a shape of the focal spot may be different.

As described above with respect to the coil diameters, a flat emitter may have a large emission area, generating a greater amount of power (e.g. a greater number of electrons) and creating a larger (e.g., wider) focal spot, or a small emission area, generating a lesser amount of power (e.g. a lesser number of electrons) and creating a smaller (e.g., narrower) focal spot.

The first emitter and the second emitter may be alternately activated to generate the first focal spot 404 and the second focal spot 406. In other words, the first electron beam may be focused on the target for a first duration, and the second electron beam may be focused on the target for a second duration. The one or more electric fields and the one or more magnetic fields may be configured in a first configuration for the first duration to generate the first focal spot 404, and the one or more electric fields and the one or more magnetic fields may be configured in a second configuration for the second duration to generate the second focal spot 406. When the composite focal spot 416 is generated by an alternation between the first focal spot 404 during the first duration and the second focal spot 406 during the second duration, due to an amount of time taken to switch from the first configuration to the second configuration, the composite focal spot 416 may be generated between two different views generated by the CT system. For example, the first focal spot 404 may be generated during a first view of the CT system, and the second focal spot 406 may be generated during a second view of the CT system. An advantage of concurrently activating the first emitter and the second emitter is that the composite focal spot 416 can have higher average power in cases where the focal spot power is target-limited.

For some types of anatomical features and/or clinical tasks, a composite focal spot within a view may be preferred. For other types of anatomical features and/or clinical tasks, a composite focal spot across two or more views may be preferred. For example, a first composite focal spot may be within a first view, where the first view has a first noise distribution. A second composite focal spot may be generated between a second view and a third view, where the second view has a second noise distribution, and the third view has a third noise distribution. If the first noise distribution is preferred by a clinician, the CT system may be configured to acquire projection data where each view of the projection data includes a composite focal spot within the view. Alternatively, if the second and/or third noise distributions are preferred by the clinician, the CT system may be configured to acquire projection data where the a composite focal spot is generated across alternating views of the projection data.

Further, additional emitters may be used to generate composite focal spots including additional focal spot components. It should be appreciated that while in FIG. 4 composite focal spot 416 includes two focal spot components (e.g., the first focal spot 404 and the second focal spot 406), in other embodiments additional focal spot components may be included. For example, composite focal spot 416 may include the first focal spot 404, the second focal spot 406, and a third focal spot, where the first focal spot 404 and the second focal spot 406 are separated by the space 415, and the second focal spot 406 and the third focal spot are separated by a second space. The third focal spot may be generated by a third set of focusing voltages on 316 and focusing currents on 324. In still other embodiments, a greater number of emitters may be used, such as 10 emitters, or 20 emitters, or a thermionic emitter array may be used, where a first set of emitters may be activated to generate a first focal spot; a second set of emitters may be activated to generate a second focal spot; a third set of emitters may be activated to generate a third focal spot; and so on.

In this way, a size and shape of the first focal spot 404 may be adjusted to a first desired size and shape; a size and shape of the second focal spot 406 may be adjusted to a second desired size and shape; and so on for additional focal spots. Additionally, a shape of the composite focal spot 416 may be configured independently of a distribution of the composite focal spot 416. In other words, the width 410 of the first focal spot 404 may be adjusted based on a first configuration of the electrostatic and/or magnetic controls of the CT system; the width 412 of the second focal spot 406 may be adjusted based on a second configuration of the electrostatic and/or magnetic controls of the CT system; and the width 414 of the space 415 may be adjusted based on a third configuration the electrostatic and/or magnetic controls of the CT system.

With respect to the single focal spot 402, an amount of power of the X-rays generated by focusing the electron beam on the target and a spatial resolution of the X-rays may depend on a size of the single focal spot 402. For example, as the size of the single focal spot 402 is decreased, the power of the X-rays may decrease and the spatial resolution of the X-rays may increase. As the size of the single focal spot 402 is increased the power of the X-rays may increase and the spatial resolution of the X-rays may decrease. Thus, the size of the single focal spot 402 may be adjusted depending on a demand for spatial resolution and/or a demand for power.

For example, a first type of anatomical feature and/or clinical task may demand a higher spatial resolution, whereby the size of the single focal spot 402 may be adjusted to a smaller size. A second type of anatomical feature and/or clinical task a demand a lower spatial resolution, whereby the size of the single focal spot 402 may be adjusted to a larger size. By adjusting the size of the single focal spot 402 to the larger size, a larger area of a scanned object (e.g., the object 328, such as an anatomical structure) may appear in focus in a view generated of the scanned object by the CT system, but with a lower spatial resolution. By adjusting the size of the single focal spot 402 to the smaller size, a smaller area of the scanned object may appear in focus, but with a higher spatial resolution.

Accordingly, in reference to the composite focal spot 416, the greater width 410 of the first focal spot 404 (e.g., with respect to the second focal spot 406) may correspond to a larger area of focus of the scanned object, while the smaller with 412 of the second focal spot 406 may correspond to a smaller area of high spatial resolution of the scanned object. By generating the composite focal spot 416 rather than the single focal spot 402, an area of the scanned object that appears in focus may be increased, due to the larger overall size of width 422 of the composite focal spot 416 compared to the single focal spot 402. A first portion of the area of the scanned object appearing in focus may be shown with a high X-ray flux (e.g., allowing small contrast differences between large objects to be more easily distinguished), corresponding to the larger, first focal spot 404. A second portion of the area of the scanned object may be shown with high spatial resolution (e.g., where features with large contrast differences may be easily distinguished and resolved), corresponding to the smaller, second focal spot 406. Thus, an advantage of generating the composite focal spot 416 as opposed to the single focal spot 402 is that a larger area of the scanned object may be in focus, while still supporting high spatial resolution within a portion of the larger area. In other words, an image may produced from a combination of projection data produced with a large focal spot, and projection data produced with a small focal spot, to balance and/or optimize both low contrast and high resolution through different parts of an acquisition of the image. In some embodiments, a configuration of the composite focal spot may be based on a prior measure of an anatomy of a patient.

FIGS. 5A-5D, 6A-6C, and 7A-7E show various exemplary distributions of electrons colliding with an target of a CT system, where the electrons are generated by one or more emitters of a cathode of the CT system in electron beams. The electron beams may be focused using electric and/or magnetic fields of the CT system, such that the electrons impinge on the target at a composite focal spot with a distribution. The composite focal spot may include two or more component focal spots, where the electrons impinging on the target at each component focal spot of the two or more component focal spots has an electron distribution, and the electron distribution of the composite focal spot is a combination of the electron distributions of the component focal spots. FIGS. 5A-5D, 6A-6C, and 7A-7E may be described in reference to the CT system 100 of FIG. 1 and/or the imaging system 200 of FIG. 2. As such, the electron beams may be the same as or similar to the electron beams 325 and 326 generated in the X-ray tube 300 of FIG. 3A, and the composite focal spot may be a non-limiting embodiment of the composite focal spot 416 of FIG. 4. FIGS. 5A-5D, 6A-6C, and 7A-7E are depicted as two dimensional plots in an X dimension, sharing a same X-axis 501. It should be appreciated that while the electron distributions of FIGS. 5A-5D are shown as two dimensional plots in the X dimension, the electron distributions may also be plotted in a Y dimension of the target, where a width of the electron distributions corresponds to a distance along a Y-axis.

Referring now to FIG. 5A, a first exemplary electron distribution graph 500 shows a first composite distribution of electrons of two electron beams impinging on an target, where the first composite distribution corresponds to a composite focal spot (e.g., composite focal spot 416). The composite focal spot may comprise two component focal spots, as described above in reference to FIG. 4. A first line 504 indicates a first electron distribution, corresponding to a first focal spot of the two component focal spots (e.g., the first focal spot 404 of FIG. 4), where the first focal spot is generated by a first electron beam (e.g., second electron beam 325). A second line 506 indicates a second electron distribution, corresponding to a second focal spot of the two component focal spots (e.g., the second focal spot 406 of FIG. 4), where the second focal spot is generated by a second electron beam (e.g., second electron beam 326). Lines 502, 504, and 506 share an X-axis 501 marked in millimeters (mm), where 0 on the X-axis 501 indicates a central reference point on the target in an X dimension.

A center of the first electron distribution indicated by the line 504 may correspond to a center of the first focal spot, indicated by a dotted line 508. A center of the second electron distribution indicated by the line 506 may correspond to a center of the second focal spot, indicated by a dotted line 510. The center of the first electron distribution may be separated from the center of the second electron distribution by a distance 512. In FIG. 5A, the center of the first electron distribution is at positioned at 0 mm on the X-axis 501, and the center of the second electron distribution is positioned at 1 mm on the X-axis 501, whereby the distance 512 is equal to 1 mm.

In FIG. 5A, apart from being offset by the distance 512, the first electron distribution is substantially similar to the second electron distribution. As a result, a size and shape of the first focal spot may be the same as a size and shape of the second focal spot (e.g., unlike the first focal spot 404 and the second focal spot 406 of FIG. 4). The first electron distribution may be a result of deflecting the first electron beam by a first distance, and the second electron distribution may be a result of deflecting the second electron beam by a second distance, where the distance 512 may be a difference between the first distance and the second distance. For example, the first distance may be 0, and the second distance may be 1.

The first exemplary electron distribution graph 500 includes a dashed line 502 indicating a first composite effective focal spot, where the first composite effective focal spot corresponds to a distribution of electrons of X-rays (generated by the first electron beam and the second electron beam colliding with the target) on a subject, such as a patient. The first composite effective focal spot may be generated by the first composite focal spot on the target, comprising the first focal spot and the second focal spot. The first composite focal spot may be indicated by a line 516 on the line 514 that intersects the composite distribution 502. The line 516 may represent a "full width half max" intensity shown pictorially in FIG. 4.

A shape of the first composite effective focal spot indicated by the line 502 may be adjusted based on a first position and dwell time during which the first electron beam is focused on the target in a first position (thereby generating the first electron distribution indicated by the line 504), a second position and dwell time during which the second electron beam is focused on the target in a second position (thereby generating the second electron distribution indicated by the line 506), and a transition time between generating the first electron beam and the second electron beam. For example, in FIG. 5A, the first composite effective focal spot indicated by the line 502 may be a result of the first dwell time being equal to the second dwell time with a finite transition time between positions.

In FIG. 5B, a second exemplary electron distribution graph 530 shows a second composite distribution of electrons of the two electron beams of FIG. 5A, where the second composite distribution is also based on the first electron distribution and position (indicated by the line 504) and the second electron distribution and position (indicated by the line 506) of FIG. 5A. FIG. 5B shares the same X-axis 501 as FIG. 5A. In FIG. 5B, a second composite effective focal spot indicated by the line 532 may be a result of the transition time being similar to the transition time of FIG. 5A, but where the first dwell time may be greater than the second dwell time As a result of the first dwell time being greater than the second dwell time, the second composite effective focal spot indicated by the line 532 is more closely aligned with the first electron distribution than the second electron distribution. Thus, by increasing the dwell time of the first electron distribution relative to the dwell time of the second electron distribution, the second composite effective focal spot may be shifted in a negative direction (e.g., to the left) on X-axis 501.

In FIG. 5C, a third exemplary electron distribution graph 550 shows a third composite distribution of electrons of the two electron beams of FIGS. 5A and 5B, where the third composite distribution is also based on the first electron distribution and position (indicated by the line 504) and the second electron distribution and position (indicated by the line 506) of FIGS. 5A and 5B. FIG. 5C shares the same X-axis 501 as FIGS. 5A and 5B. In FIG. 5C, a third composite effective focal spot indicated by the line 552 may be a result of the same equal dwell time as FIG. 5A, but where the transition is blanked so that no electrons are emitted during the transition. The size of the third composite effective focal spot indicated by the line 552 may be greater than the first composite effective focal spot of FIG. 5A because fewer electrons impinge the target between the two positions, thus reducing the peak intensity at the center of the composite beam which effectively widens the beam.

In FIG. 5D, a fourth exemplary electron distribution graph 580 shows a fourth composite distribution of electrons of the two electron beams of FIGS. 5A, 5B, and 5C, where the fourth composite distribution is also based on the first electron distribution (indicated by the line 504) and the second electron distribution (indicated by the line 506) of FIGS. 5A, 5B, and 5C. FIG. 5D shares the same X-axis 501 as FIGS. 5A, 5B, and 5C. In FIG. 5D, a fourth composite effective focal spot indicated by the line 582 may be a result of a first dwell time of the first electron distribution being greater than a second dwell time of the second electron distribution, as in FIG. 5B, and where the transition is blanked between the first electron distribution and the second electron distribution as in FIG. 5C. The fourth composite effective focal spot may have an electron distribution that is skewed towards the first electron distribution indicated by line 504, yet covering a full extent of the second electron distribution indicated by the line 506 along the X-axis 501.

While FIGS. 5A-5C show various exemplary distributions of electrons of composite effective focal spots comprising a first electron distribution and a second electron distribution of the same shape, where the first electron distribution and the second electron distribution are centered at different positions on the X-axis 501, FIGS. 6A-6C show various exemplary distributions of electrons of composite effective focal spots comprising a first electron distribution and a second electron distribution, where the first electron distribution and the second electron distribution are centered at the same position 0 on the X-axis 501, but have different shapes and/or sizes.

Referring now to FIG. 6A, a first exemplary electron distribution graph 600 shows a first composite distribution of electrons of two electron beams impinging on an target, where the first composite distribution corresponds to a composite focal spot. The composite focal spot may comprise two component focal spots, as described above in reference to FIG. 4. A first line 604 indicates a first electron distribution, corresponding to a first focal spot of the two component focal spots (e.g., the first focal spot 404 of FIG. 4), where the first focal spot is generated by a first electron beam (e.g., second electron beam 325). A second line 606 indicates a second electron distribution, corresponding to a second focal spot of the two component focal spots (e.g., the second focal spot 406 of FIG. 4), where the second focal spot is generated by a second electron beam (e.g., second electron beam 326).

In FIG. 6A, the first electron distribution 604 may be a result of focusing the first electron beam in accordance with a first configuration of electrostatic and/or electromagnetic controls of the CT system, and the second electron distribution 606 may be a result of focusing the second electron beam in accordance with a second configuration of electrostatic and/or electromagnetic controls of the CT system. For example, the first configuration of the electrostatic and/or electromagnetic controls may generate a broad electron distribution, and the second configuration of the electrostatic and/or electromagnetic controls may generate a narrow electron distribution.

The first exemplary electron distribution graph 600 includes a dashed line 602 indicating a first composite effective focal spot, where the first composite effective focal spot corresponds to a distribution of electrons of X-rays (generated by the first electron beam and the second electron beam colliding with the target) on a subject, such as a patient. The first composite effective focal spot may be generated by the first composite focal spot on the target, comprising the first focal spot and the second focal spot. The first composite focal spot may be indicated by a line 614 that intersects the composite distribution 602 (indicated by the line 616) The first focal spot and the second focal spot may both be centered at the same point 0 of the X-axis 501. In FIG. 6A, the first focal spot indicated by the line 616 may be large (e.g., wide in the X dimension) focal spot, and the second focal spot indicated by the line 618 may be small (e.g., narrow in the X dimension) focal spot. Thus, the first focal spot may correspond to a larger area of focus of an image generated by the X-rays, and the second focal spot may correspond to a smaller area within (e.g., at the center of) the larger area, where the smaller area may have a higher spatial resolution than the larger area.

A shape of the first composite effective focal spot indicated by the line 602 may be adjusted based on a first dwell time during which the first electron beam is focused on the target (thereby generating the first electron distribution indicated by the line 604), a second dwell time during which the second electron beam is focused on the target (thereby generating the second electron distribution indicated by the line 606), and a transition time between generating the first electron beam and the second electron beam. For example, in FIG. 6A, the first composite effective focal spot indicated by the line 602 may be a result of the first dwell time being equal to the second dwell time, where the electron distribution of the first composite effective focal spot is centered between the first electron distribution and the second electron distribution.

In FIG. 6B, a second exemplary electron distribution graph 630 shows a second composite distribution of electrons of the two electron beams of FIG. 6A, where the second composite distribution is also based on the first electron distribution (indicated by the line 604) and the second electron distribution (indicated by the line 606) of FIG. 6A. FIG. 6B shares the same X-axis 501 as FIG. 6A. In FIG. 6B, a second composite effective focal spot indicated by the line 632 may be a result of the second dwell time being greater than the first dwell time by a large margin. As a result of the second dwell time being greater than the first dwell time, the second composite effective focal spot indicated by the line 632 is more closely aligned with the second electron distribution than the first electron distribution.

In FIG. 6C, a third exemplary electron distribution graph 650 shows a third composite distribution of electrons of the two electron beams of FIGS. 6A and 6B, where the third composite distribution is also based on the first electron distribution (indicated by the line 604) and the second electron distribution (indicated by the line 606) of FIG. 6A. FIG. 6C shares the same X-axis 501 as FIGS. 6A and 6B. In FIG. 6C, a third composite effective focal spot indicated by the line 652 may be a result of the blanking the beam during the transition time and having the second dwell time being greater than the first dwell time as in FIG. 6B. Thus, by both reducing electrons during the transition from the wider to the smaller focal spot and increasing the dwell time of the second electron distribution relative to the dwell time of the first electron distribution, a shape of the second composite effective focal spot may be adjusted to more closely match the shape of the second electron distribution.

FIGS. 7A-7D show various exemplary distributions of electrons of composite effective focal spots comprising a first electron distribution 704 and a second electron distribution 706. The first electron distribution 704 may be a result of focusing a first electron beam in accordance with a first configuration of electrostatic and/or electromagnetic controls of the CT system, and the second electron distribution 706 may be a result of focusing a second electron beam in accordance with a second configuration of electrostatic and/or electromagnetic controls of the CT system, as described above. In FIGS. 7A-7D, the first electron distribution and the second electron distribution are focused at different positions on the X-axis 501 (as in FIGS. 5A-5D), and additionally have different shapes and/or sizes (as in FIGS. 6A-6C). As a result of the first electron distribution and the second electron distribution being focused at different positions on the X-axis 501 and having different shapes and/or sizes, the composite effective focal spots depicted in FIGS. 7A-7D are based on a larger (e.g., wider) first focal spot generated by the first electron distribution, and a smaller (e.g., narrower) second focal spot generated by the second electron distribution, where the second focal spot is offset from the first focal spot in the X dimension. Thus, the first focal spot and the second focal spot may be similar to the first focal spot 404 and the second focal spot 406 of FIG. 4. Additionally, the first focal spot may be separated from the second focal spot by a spacing (e.g., the space 415 of FIG. 4).

Referring now to FIG. 7A, a first line 704 indicates a first electron distribution, corresponding to the first focal spot. A second line 706 indicates a second electron distribution, corresponding to the second focal spot. Lines 704 and 706 share the X-axis 501, where 0 on the X-axis 501 indicates the central reference point on the target in the X dimension.

The first exemplary electron distribution graph 700 includes a dashed line 702 indicating a first composite effective focal spot, where the first composite effective focal spot corresponds to a distribution of electrons of X-rays (generated by the first electron beam and the second electron beam colliding with the target) on a subject, such as a patient. The first composite effective focal spot may be generated by a first composite focal spot on the target, comprising the first focal spot and the second focal spot. The first composite focal spot may be indicated on a line 714 that intersects the composite distribution, with a first focal spot indicated by a line 716 and a second focal spot indicated by a line 718. The composite focal spot indicated by lines 716 and 718 may be separated by a spacing 720, similar to the spacing 415 of the composite focal spot 416 of FIG. 4. In FIG. 7A, the first focal spot indicated by the line 716 may be a large (e.g., wide in the X dimension) focal spot, and the second focal spot indicated by the line 718 may be a small (e.g., narrow in the X dimension) focal spot. Thus, the first focal spot may correspond to a larger area of focus of an image generated by the X-rays, and the second focal spot may correspond to a smaller area (offset in the X dimension from the larger area), where the smaller area may have a higher spatial resolution than the larger area.

A shape of the first composite effective focal spot indicated by the line 702 may be adjusted based on a first dwell time during which the first electron beam is focused on the target (thereby generating the first electron distribution indicated by the line 704), a second dwell time during which the second electron beam is focused on the target (thereby generating the second electron distribution indicated by the line 706), and a transition time between generating the first electron beam and the second electron beam. For example, in FIG. 7A, the first composite effective focal spot indicated by the line 702 may be a result of equal dwell times and finite transition period where electrons impinge the target between the first and second spots.

In FIG. 7B, a second exemplary electron distribution graph 730 shows a second composite distribution of electrons of the two electron beams of FIG. 7A, where the second composite distribution is also based on the first electron distribution (indicated by the line 704) and the second electron distribution (indicated by the line 706) of FIG. 7A. FIG. 7B shares the same X-axis 501 as FIG. 7A. In FIG. 7B, a second composite effective focal spot indicated by the line 732 may be a result of the second spot having an greater dwell time than the first spot. This creates a composite focal spot that has a more less pronounced first lobe.

In FIG. 7C, a third exemplary electron distribution graph 750 shows a third composite distribution of electrons of the two electron beams of FIGS. 7A and 7B, where the third composite distribution is also based on the first electron distribution (indicated by the line 704) and the second electron distribution (indicated by the line 706) of FIGS. 7A and 7B. FIG. 7C shares the same X-axis 501 as FIGS. 7A and 7B. In FIG. 7C, a third composite effective focal spot indicated by the line 752 may be a result of uniform dwell time as FIG. 7A, but blanking of the beam during the transition. This creates a composite focal spot that resembles the first and second, with no x-rays generated during the transition.

In FIG. 7D, a fourth exemplary electron distribution graph 760 shows a fourth composite distribution of electrons of the two electron beams of FIGS. 7A, 7B, and 7C, where the fourth composite distribution is also based on the first electron distribution (indicated by the line 704) and the second electron distribution (indicated by the line 706) of FIGS. 7A, 7B, and 7C. FIG. 7D shares the same X-axis 501 as FIGS. 7A, 7B, and 7C. In FIG. 7D, a fourth composite effective focal spot indicated by the line 762 may be a result of the dwell time of the second focal spot being greater than then first as in FIG. 7B and the transition blanked as in FIG. 7C. This results in a composite focal spot that underweights the wider portion relative to the narrow portion.

Referring now to FIG. 7E, a fifth exemplary electron distribution graph 770 shows a fifth composite distribution of electrons of the two electron beams of FIGS. 7A, 7B, 7C, and 7D, where the fifth composite distribution is based on a first electron distribution indicated by a line 774 and a second electron distribution indicated by a line 776. In FIG. 7E, the first electron distribution includes a first side lobe 778, at a first (e.g., left) edge 786 of the first electron distribution, and a second side lobe 780, at a second (e.g., right) edge 788 of the first electron distribution. Similarly, the second electron distribution includes a first side lobe 782, at a first (e.g., left) edge 790 of the second electron distribution, and a second side lobe 784, at a second (e.g., right) edge 792 of the second electron distribution. The side lobes 778, 780 of the first electron distribution may be a result of focusing the first electron beam via electrostatic controls and/or electromagnetic controls of the CT system to narrow and parallelize a Gaussian distribution of electrons of the first electron beam. The side lobes 782, 784 of the second electron distribution may be a result of focusing the second electron beam via the electrostatic controls and/or electromagnetic controls, to narrow and parallelize a Gaussian distribution of electrons of the second electron beam. Generation of side lobes is described in greater detail in reference to FIG. 8.

Figure 8:
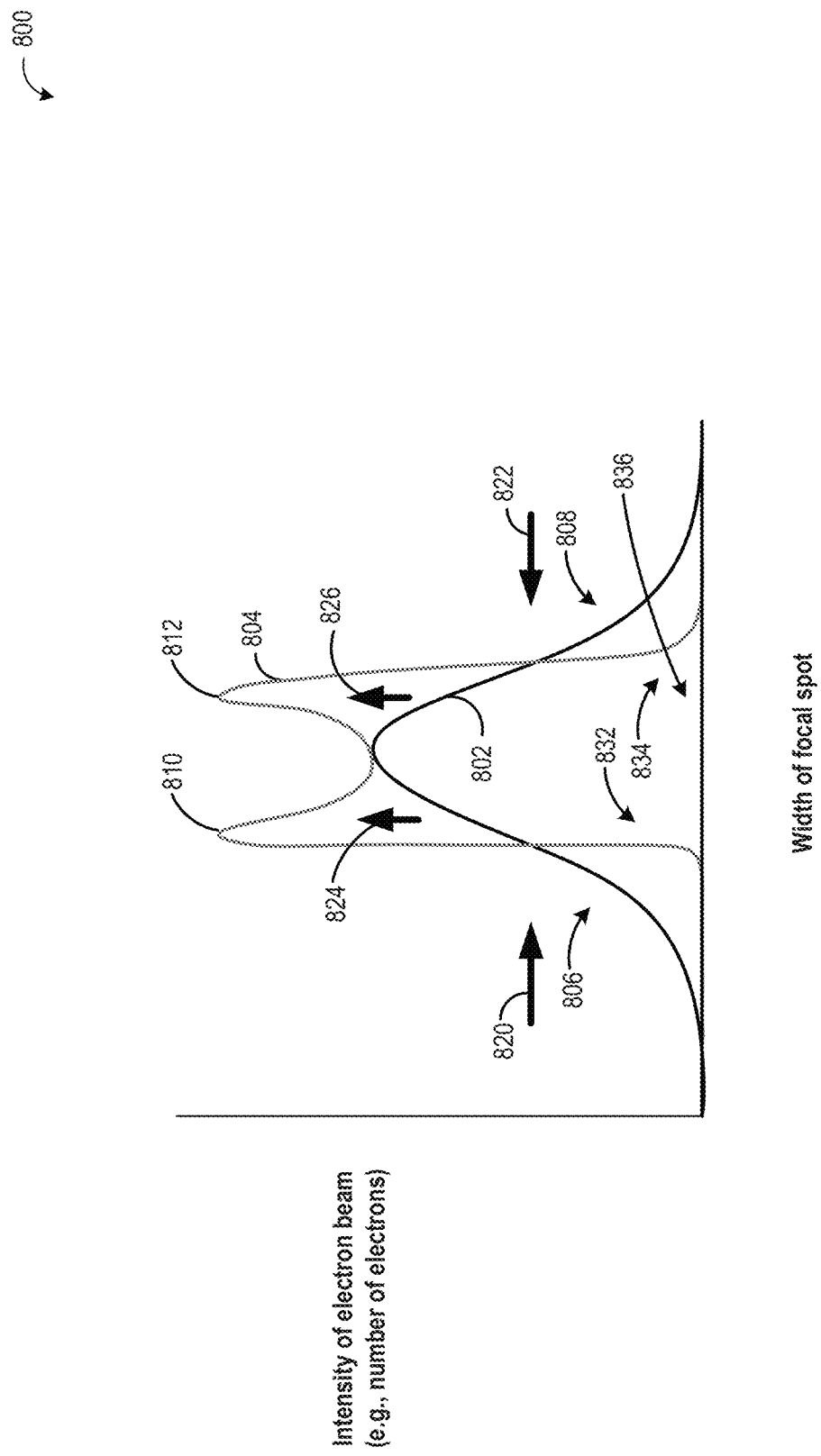
FIG. 8 shows a plot of a Gaussian electron distribution of a focal spot including side lobes, in accordance with one or more embodiments of the present disclosure.

Referring briefly to FIG. 8, a side lobe diagram 800 shows a plot of a Gaussian electron distribution 802 of a focal spot, where an X-axis of the plot indicates a distribution of electrons colliding with an target along an X dimension (e.g., along a width of the focal spot), and a Y-axis of the plot indicates a number of electrons colliding with the target at a corresponding point on the X-axis (e.g., an intensity of the focal spot). The Gaussian electron distribution 802 may be a result of applying electrostatic controls and/or electromagnetic controls to focus an electron beam on an target (e.g., the electron beam 312 and target 304 of FIG. 3A). The electrostatic controls and/or electromagnetic controls may generate one or more electric fields and/or one or more magnetic fields. The one or more electric fields and/or one or more magnetic fields may apply a first force on the electrons of the electron beam towards a center of the Gaussian electron distribution 802 in a first direction indicated by an arrow 820, and a second force on the electrons of the electron beam towards a center of the Gaussian electron distribution 802 in a second direction indicated by an arrow 822. As a result of the first force and the second force, electrons on a first edge 806 and a second edge 808 of the Gaussian distribution may be redirected inwards towards a center of the Gaussian distribution. By redirecting the electrons on the first edge 806 and the second edge 808 inwards towards the center, a shape of the Gaussian distribution may be altered, whereby sides of the Gaussian distribution 802 may be inverted, resulting in sides that approximate parallel lines.

As a result of the electrons being directed inwards, more electrons of the electron beam may collide with the target at a first edge 832 and a second edge 834 of the Gaussian distribution 802 than at the center of the Gaussian distribution 802, as indicated by a first side lobe 810 at a left side of the Gaussian distribution 802 and a second side lobe 812 at a right side of the Gaussian distribution 802. The greater number of electrons colliding with the target at the first edge 832 and the second edge 834 may result in a composite focal spot 836.

Returning now to FIG. 7E, a fifth composite effective focal spot indicated by the line 772 may be generated from a composite focal spot comprising a first focal spot based on the first electron distribution indicated by line 774, and a second focal spot based on the second electron distribution indicated by line 776. The fifth composite effective focal spot indicated by the line 772 may be a result of adjusting any of the dwell times, transition times, and transition blanking as described in FIGS. 5A-5D, 6A-6C, and 7A-7D. As with FIGS. 5A-5D, 6A-6C, and 7A-7D, the fifth composite effective focal spot indicated by the line 772 may be generated by a fifth composite focal spot indicated by a line 796, on a line 794 that intersects the composite distribution.

Figure 9:
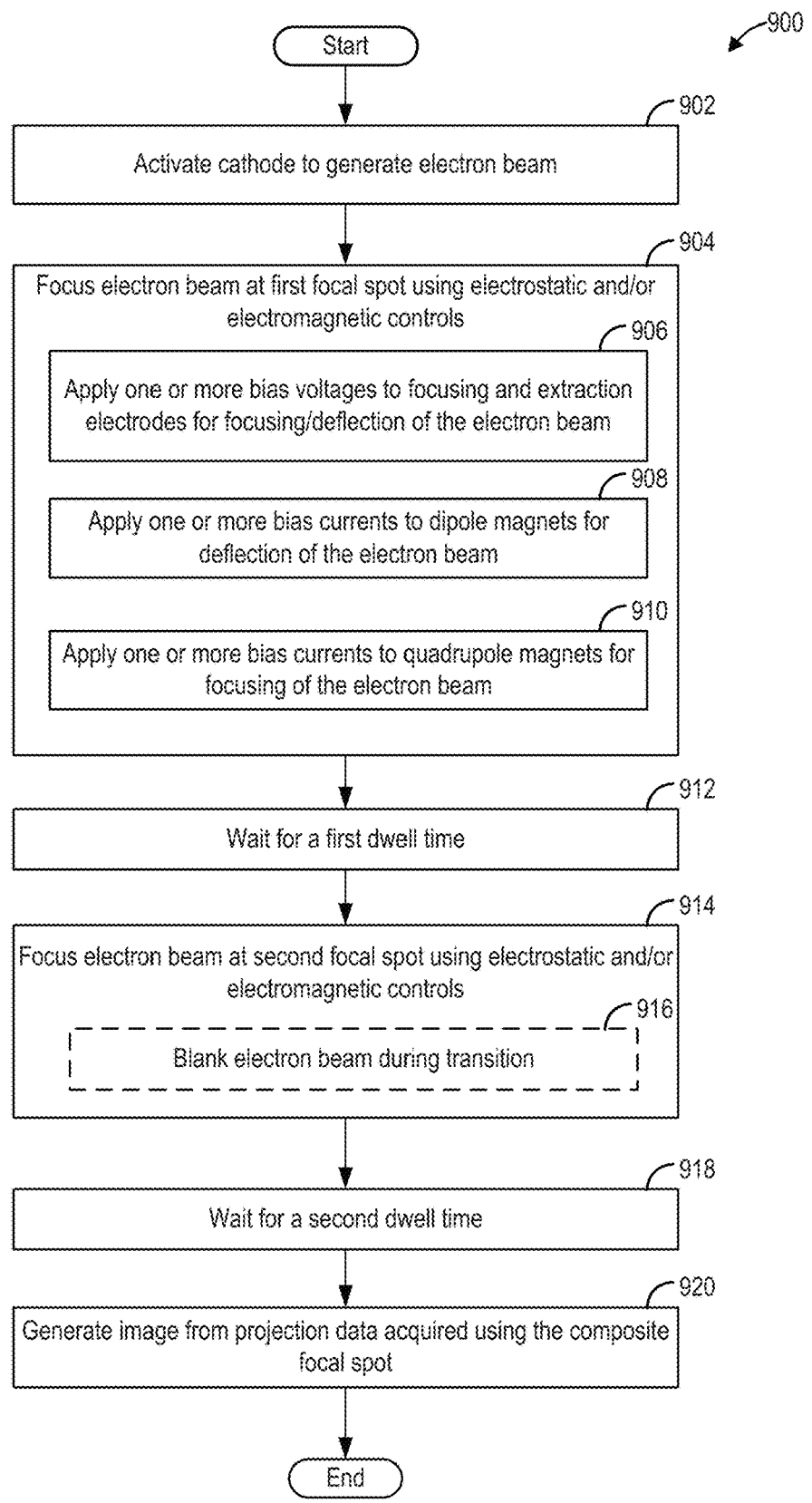
FIG. 9 is a flowchart illustrating an exemplary method for generating a composite focal spot comprising a first focal spot and a second focal spot, in accordance with one or more embodiments of the present disclosure.

Referring now to FIG. 9, an example method 900 is shown for generating an image from projection data acquired using a composite focal spot comprising a first focal spot and a second focal spot, by alternately activating an emitter of a cathode of a CT system. Method 900 is described in reference to the CT system 100 of FIG. 1 and/or the imaging system 200 of FIG. 2, where the cathode may be a non-limiting embodiment of the cathode 302 of X-ray tube 300 of FIG. 3A. Method 900 may be executed by a processor of a controller of the CT system, such as processor of control electronics module 322 of FIG. 3A, in response to instructions provided by an operator of the CT system and/or stored in a memory of the CT system.

Method 900 begins at 902, where method 900 includes activating the cathode of the CT system to generate an electron beam, as described above in reference to the electron beam 312 of FIG. 3A. The electron beam may be directed towards an target (e.g., target 304) of the CT system, where electrons of the electron beam may collide with the target to generate X-rays that may be directed at an object (e.g., object 328).

At 904, method 900 includes focusing the electron beam at a first focal spot on the target, using electrostatic and/or electromagnetic controls. The first focal spot may be the same as or similar to the first focal spot 404 of FIG. 4.

At 906, focusing the electron beam at a first focal spot includes applying one or more voltages to one or more corresponding extraction and focusing electrodes of the X-ray tube (e.g., the one or more focusing electrodes 316 of FIG. 3A). In various embodiments, a first set of the one or more corresponding focusing electrodes may perform a first deflection of the electron beam, and a second set of the one or more corresponding focusing electrodes may perform a first focusing of the electron beam.

Performing the first deflection of the electron beam may include shifting a position of the electron beam in a dimension. For example, a first configuration of voltages applied to the first set of the one or more corresponding focusing electrodes may generate electric fields that shift the electron beam in an X dimension (e.g., to a patient's left or right side), and a second configuration of voltages applied to the first set of the one or more corresponding focusing electrodes may generate electric fields (e.g., the one or more electric fields 320 of FIG. 3A) that shift the electron beam in a Z dimension (e.g., to a top or bottom of a patient). A number of electric fields generated may correspond to a number of focusing electrodes receiving voltages. For example, the first configuration may include applying a voltage to a first focusing electrode, but not applying a voltage to a second focusing electrode. The second configuration may include applying a voltage to the second focusing electrode, but not applying a voltage to the first focusing electrode. By applying the voltages to select focusing electrodes of the one or more focusing electrodes, a desired number of electric fields may be generated. Further, by adjusting each voltage of the voltages, a magnitude of each electric field of the desired number of electric fields may be controlled. Each electric field may apply a force to electrons of the electron beam, causing a position of the electrons forming the electric beam to shift in a desired direction. Thus, a position of the focal spot generated by the electron beam may be adjusted to a desired position by deflecting the electron beam.

Performing the first focusing of the electron beam may include altering a shape of the focal spot created by the electron beam. For example, a first configuration of voltages applied to the second set of the one or more corresponding focusing electrodes may generate electric fields that focus the electron beam to create a focal spot of a first shape, and a second configuration of voltages applied to the second set of the one or more corresponding focusing electrodes may generate electric fields that focus the electron beam to create a focal spot of a second shape. For example, the first shape and the second shape may be rectangular shapes, where the first shape has a first, larger width, and the second shape has a second, narrower width (e.g., as described above in reference to the first focal spot 404 and the second focal spot 406 of FIG. 4). By applying different voltages to select focusing electrodes of the second set of the one or more corresponding focusing electrodes, a desired number of electric fields may be generated that focus the electron beam to a desired shape and/or size.

At 908, focusing the electron beam at the first focal spot using the electrostatic and/or electromagnetic controls further comprises applying one or more currents to one or more respective dipole magnets of the X-ray tube (e.g., the one or more magnets 324 of FIG. 3A) to perform a second deflection of the electron beam. In various embodiments, the one or more dipole magnets may be positioned within the X-ray tube to generate a force in the same dimension as the first deflection. More specifically, when the one or more currents are applied to the one or more respective dipole magnets, a respective number of magnetic fields (e.g., the one or more magnetic fields 323 of FIG. 3A) may each generate a force on the electron beam, which may further adjust the deflection of the electron beam in the same dimension as the first deflection. The second deflection may be larger and/or more precise than the first deflection, due to a greater strength of the magnetic fields with respect to the electric fields. In other words, the first deflection of the electron beam performed by the focusing electrodes may not be sufficient to deflect the first focal spot to a desired position (e.g., due to a length of the X-ray tube), whereby the second, additional deflection performed by the dipole magnets may be sufficient to deflect the first focal spot to the desired position.

At 910, focusing the electron beam at the first focal spot using the electrostatic and/or electromagnetic controls further comprises applying one or more currents to one or more respective quadrupole magnets of the X-ray tube (e.g., the one or more magnets 324 of FIG. 3A) to perform a second focusing of the electron beam. When the one or more currents are applied to the one or more respective quadrupole magnets, a respective number of magnetic fields (e.g., the one or more magnetic fields 323 of FIG. 3A) may each generate a force on the electron beam in two dimensions, which may focus the electron beam. The second focusing may be larger and/or more precise than the first focusing, due to a greater strength of the magnetic fields generated by the quadrupole magnets with respect to the electric fields. In other words, the first focusing of the electron beam performed by the focusing electrodes may not be sufficient to focus the first focal spot to a desired shape and/or size (e.g., due to a length of the X-ray tube), whereby the second, additional focusing performed by the quadrupole magnets may be sufficient to focus the first focal spot to the desired shape and/or size.

It should be appreciated that steps 906, 908, and 910 of method 900 may be applied concurrently, or in a different order than presented above.

At 912, method 900 includes waiting for a first dwell time. The first dwell time is a first duration during which the electron beam is deflected and focused to generate the first focal spot at a desired position, shape, and size, by a combination of the one or more electric fields generated by the focusing electrodes and the one or more magnetic fields generated by the dipole and quadrupole magnets.

At 914, method 900 includes focusing the electron beam at a second focal spot via electrostatic and/or electromagnetic controls. The second focal spot may be the same as or similar to the second focal spot 406 of FIG. 4. Refocusing the electron beam at the second focal spot may include adjusting a configuration of the electrostatic and/or electromagnetic controls. For example, focusing the electron beam at the first focal spot may include adjusting the electrostatic and/or electromagnetic controls to a first configuration. Adjusting the electrostatic and/or electromagnetic controls to the first configuration may include adjusting a first power delivered to the focusing electrodes, and/or adjusting a second power delivered to the one or more dipole magnets and the one or more quadrupole magnets of the X-ray tube. The first power may be greater than the second power, where a greater amount of energy is delivered to the focusing electrodes than the dipole and quadrupole magnets, or the second power may be greater than the first power, where a greater amount of energy is delivered to the dipole and quadrupole magnets than the focusing electrodes. Further, the second power may be divided and/or balanced between a number of magnets or poles of the one or more magnets. For example, the second power may be distributed between four poles of a quadrupole magnet to generate one or more magnetic fields, the one or more magnetic fields having a desired strength and/or a desired direction. By adjusting the distribution of the second power between the four poles, the electron be may be deflected and/or focused to produce the first focal spot.

After the first duration has ended, the electrostatic and/or electromagnetic controls may be adjusted from the first configuration to a second configuration, where the second configuration focuses the electron beam at the second focal spot. Adjusting the electrostatic and/or electromagnetic controls from the first configuration to the second configuration may include adjusting either or both of the first power of the second power, and/or adjusting a distribution of the second power between the magnets or poles of the one or more dipole magnets and/or the one or more quadrupole magnets.

At 916, refocusing the electron beam at the second focal spot via electrostatic and/or electromagnetic controls may optionally include blanking the electron beam during a transition between focusing the electron beam at the first focal spot and refocusing the electron beam at the second focal spot. In various embodiments, blanking the electron beam may be achieved by switching the emitter of the cathode off during the transition. For example, the emitter may be switched on for a first duration, where the first duration is the first dwell time. At the end of the first duration, the emitter may be switched off for a second duration, where no electrons are directed at the target. At the end of the second duration, the emitter may be switched on for a third duration, where the third duration is a second dwell time.

At 918, method 900 includes waiting for the second dwell time, during which the electron beam is focused at the second focal spot. The second dwell time may be the same as the first dwell time, or the second dwell time may be different from the first dwell time. For example, in some embodiments, the first dwell time may be of a shorter duration, and the second dwell time may be of a longer duration, while in other embodiments, the first dwell time may be of a longer duration, and the second dwell time may be of a shorter duration. As described above in reference to FIGS. 5A-7E, the first dwell time and the second dwell time may be controlled to create a composite focal spot of a desired shape, size, and position.

At 920, method 900 includes generating an image from projection data acquired using the composite focal spot, and method 900 ends.

Thus, methods and systems are proposed herein for generating a composite focal spot comprising a first focal spot of a first size and shape, at a first position, and a second focal spot of a second size and shape, at a second position, where the second size, shape and position may be different from the first size, shape, and position. Images generated using the composite focal spot may include a large area of focus, with a portion of the image in a high spatial resolution, thereby combining advantages of using a smaller focal spot with advantages of using a larger focal spot. The size and shape of the first focal spot and the second focal spot may be individually configured based on a desired profile of the composite focal spot. The composite focal spot may be generated by alternating between focusing the electron beam on the first focal spot and the second focal spot, or by concurrently activating a plurality of emitters of a cathode of the CT system. The composite focal spot may be generated within a view acquired by the CT system, or between views acquired by the CT system. By using a composite focal spot, an overall size of an area of focus in images generated by the CT system may be increased, with a first portion of the area of focus where smaller contrast differences may be distinguished, and a second portion of the area of focus where larger contrast differences may be distinguished, resulting in a higher quality image. A further advantage of the systems and methods described herein is that the composite focal spot may be configured using software, while relying on existing hardware configurations of X-ray tubes of the CT system.

The technical effect of creating a composite focal spot from two component focal spots is that a quality of an image generated using the composite focal spot may be increased with respect to using a single focal spot.

The disclosure also provides support for a method for a computed tomography (CT) system, comprising: controlling the CT system to focus a beam of electrons generated by a cathode of the CT system at a plurality of focal spots on a surface of an target of the CT system, generating a composite focal spot from the plurality of focal spots, and obtaining projection data of the CT system with the composite focal spot. In a first example of the method, generating the composite focal spot from the plurality of focal spots further includes generating the composite focal spot based on at least one of: a shape of each focal spot of the plurality of focal spots, a position of each focal spot of the plurality of focal spots, a dwell time of each focal spot of the plurality of focal spots, and a transition time between each focal spot of the plurality of focal spots. In a second example of the method, optionally including the first example, a number of focal spots of the plurality of focal spots is two. In a third example of the method, optionally including one or both of the first and second examples, a width of the composite focal spot in an X dimension is larger than a sum of a width of a first focal spot of the plurality of focal spots along the X dimension and a width of a second focal spot of the plurality of focal spots along the X dimension, and the width of the first focal spot is greater than the width of the second focal spot. In a fourth example of the method, optionally including one or more or each of the first through third examples, controlling the CT system to focus a beam of electrons at the two focal spots further comprises: adjusting controls of the CT system to focus the beam of electrons at the first focal spot for a first dwell time, adjusting the controls of the CT system to focus the beam of electrons at the second focal spot for a second dwell time, the second dwell time starting after the first dwell time ends, and responsive to a transition time between focusing the beam of electrons at the first focal spot and focusing the beam of electrons at the second focal spot exceeding a threshold transition time, switching off the beam of electrons between the first dwell time and the second dwell time. In a fifth example of the method, optionally including one or more or each of the first through fourth examples, adjusting the controls of the CT system further comprises adjusting at least one of electrostatic controls and/or electromagnetic controls of the CT system, where adjusting the electrostatic controls includes adjusting one or more voltages delivered at one or more electrodes of the CT system, and adjusting the electromagnetic controls includes adjusting one or more currents delivered to one or more magnets of the CT system. In a sixth example of the method, optionally including one or more or each of the first through fifth examples, the composite focal spot is generated within a view of the projection data of the CT system. In a seventh example of the method, optionally including one or more or each of the first through sixth examples, the composite focal spot is generated between views of the projection data. In an eighth example of the method, optionally including one or more or each of the first through seventh examples, the cathode includes a plurality of emitters, and a number of focal spots is generated by activating a respective number of emitters. In a ninth example of the method, optionally including one or more or each of the first through eighth examples, the plurality of emitters further includes a first emitter with a first filament of a first size, and a second emitter with a second filament of a second size, where a first focal spot is generated by the first emitter and a second focal spot is generated by the second emitter. In a tenth example of the method, optionally including one or more or each of the first through ninth examples, the composite focal spot includes a first focal spot at a first edge of the composite focal spot, and a second focal spot at a second edge of the composite focal spot, where the first focal spot and the second focal spot are generated by focusing the beam of electrons to adjust a distribution of electrons of the beam of electrons from an approximately Gaussian electron distribution to an electron distribution having side lobes.

The disclosure also provides support for a computed tomography (CT) system, comprising: an X-ray tube including a cathode and a target, and an X-ray controller including one or more processors having executable instructions stored in a non-transitory memory of the CT system that, when executed, cause the one or more processors to: focus a first electron beam generated by the cathode at a first focal spot on the target, based on a first configuration of electrostatic controls and/or electromagnetic controls of the X-ray controller, focus a second electron beam generated by the cathode at a second focal spot on the target, based on a second configuration of electrostatic controls and/or electromagnetic controls of the X-ray controller, and acquire an image of an object from projection data acquired based on a composite focal spot comprising the first focal spot and the second focal spot. In a first example of the system, focusing the first electron beam based on the first configuration of electrostatic controls and/or electromagnetic controls further comprises delivering a first set of voltages to one or more respective electrodes of the X-ray tube, and/or one or more respective dipole magnets of the X-ray tube, and/or one or more respective quadrupole magnets of the X-ray tube, and focusing the second electron beam based on the second configuration of electrostatic controls and electromagnetic controls further comprises delivering a second set of voltages to one or more respective electrodes of the X-ray tube, and/or one or more respective dipole magnets of the X-ray tube, and/or one or more respective quadrupole magnets of the X-ray tube. In a second example of the system, optionally including the first example, the first electron beam is generated by a first set of one or more emitters of the cathode, the first set of one or more emitters generating a first size and shape of the first focal spot, and the second electron beam is generated by a second, different set of one or more emitters of the cathode, the second, different set of one or more emitters generating a second size and shape of the second focal spot, the first size and shape different from the second size and shape. In a third example of the system, optionally including one or both of the first and second examples, the first electron beam is deflected to a first desired position on the target and focused for a first duration, and the second electron beam is deflected to a second desired position on the target and focused for a second duration, the second duration starting after an end of the first duration. In a fourth example of the system, optionally including one or more or each of the first through third examples, the first electron beam and the second electron beam are a single electron beam, and the first focal spot is generated by directing electrons at a first edge of a Gaussian distribution of electrons of the single electron beam towards a center of the Gaussian distribution based on the first configuration of electrostatic controls and/or electromagnetic controls, and the second focal spot is generated by directing electrons at a second edge of a Gaussian distribution of electrons of the single electron beam towards a center of the Gaussian distribution based on the second configuration of electrostatic controls and electromagnetic controls.

The disclosure also provides support for a method for a computed tomography (CT) system, comprising: focusing a first beam of electrons generated by a cathode of the CT system at a first focal spot on a surface of a target of the CT system, focusing a second beam of electrons generated by the cathode at a second focal spot on the surface of the target, generating a composite focal spot on the target comprising the first focal spot and the second focal spot, and generating an image from projection data of the CT system acquired using the composite focal spot, the image including an area of focus corresponding to the composite focal spot, the area of focus including a larger area of high X-ray flux where small contrast differences between large objects are better distinguished, corresponding to the first focal spot, and a smaller area of high spatial resolution where large contrast differences between small objects are better distinguished, corresponding to the second focal spot. In a first example of the method, generating the composite focal spot further comprises generating the composite focal spot based on at least one of: a first deflection of the first beam of electrons and a second deflection of the second beam of electrons, a first dwell time of the first beam of electrons at the first focal spot and a second dwell time of the second beam of electrons at the second focal spot, a first width of the first focal spot and a second width of the second focal spot in a dimension, a first shape of a first distribution of electrons at the first focal spot and a second shape of a second distribution of electrons at the second focal spot, and a transition time between focusing the first beam of electrons at the first focal spot and focusing the second beam of electrons at the second focal spot. In a second example of the method, optionally including the first example, the first beam of electrons is generated by a first set of one or more emitters of the cathode, the second beam of electrons is generated by a second set of the one or more emitters of the cathode, and the first beam of electrons is generated concurrently with the second beam of electrons. In a third example of the method, optionally including one or both of the first and second examples, generating the first beam of electrons concurrently with the second beam of electrons further includes at least one of: initiating the first beam of electrons prior to initiating the second beam of electrons, initiating the second beam of electrons prior to initiating the first beam of electrons, terminating the first beam of electrons prior to terminating the second beam of electrons, and terminating the second beam of electrons prior to terminating the first beam of electrons.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for a computed tomography (CT) system, comprising:
controlling an X-ray source of the CT system to create a desired distribution of electrons striking a target of the CT system at each view of a subject, the desired distribution forming a composite focal spot, the composite focal spot including a first focal spot having a first distribution of electrons striking the target and a second focal spot having a second distribution of electrons striking the target, wherein a center of the first focal spot is separated from a center of the second focal spot;
obtaining projection data from X-rays generated as a result of electrons of the desired distribution of electrons striking the target; and
reconstructing an image from the projection data.

2. The method of claim 1, wherein the first focal spot and the second focal spot differ with respect to at least one of:
a size of each focal spot;
a shape of each focal spot;
a position of each focal spot;
a dwell time of each focal spot; and
a transition time between each focal spot.

3. The method of claim 2, wherein the first focal spot has a first width in an X dimension, and the second focal spot has a second width in the X dimension, and a width of the composite focal spot in the X dimension is larger than a sum of the first width and the second width.

4. The method of claim 2, wherein the composite focal spot includes the first focal spot at a first edge of the composite focal spot, and the second focal spot at a second edge of the composite focal spot, and the desired distribution of electrons includes side lobes.

5. The method of claim 1, further comprising electrostatically and/or magnetically controlling a beam of electrons to alternate between a first electron beam that impinges on the target at the first focal spot for a first dwell time, and a second electron beam that impinges on the target at the second focal spot for a second dwell time, the second dwell time starting after the first dwell time ends, within a single view acquired by the CT system.

6. The method of claim 5, wherein electrostatically and/or magnetically controlling the beam of electrons to alternate between the first electron beam that impinges on the target at the first focal spot for the first dwell time, and the second electron beam that impinges on the target at the second focal spot for the second dwell time further comprises:
switching off the beam of electrons between the first dwell time and the second dwell time.

7. The method of claim 6, wherein the desired distribution of electrons striking the target and forming the composite focal spot generates a composite effective focal spot on the subject of the CT system, and a shape of the composite effective focal spot is determined by the first dwell time, the second dwell time, and a transition time between the first dwell time and the second dwell time.

8. The method of claim 7, further comprising increasing the first dwell time relative to the second dwell time to adjust a shape of the composite effective focal spot to match a shape of the first electron distribution of the first focal spot.

9. The method of claim 8, further comprising adjusting the shape of the composite effective focal spot in a Z dimension, the Z dimension aligned with a length of the subject.

10. The method of claim 7, wherein the second electron distribution is a narrower electron distribution than the first electron distribution, and the method further comprises increasing a spatial resolution of the composite effective focal spot by increasing the second dwell time relative to the first dwell time.

11. The method of claim 1, wherein the desired distribution of electrons striking the target of the CT system forming the composite focal spot is generated both within a view of the projection data of the CT system and between consecutive views acquired by the CT system.

12. The method of claim 1, wherein a cathode of the CT system includes a plurality of emitters, and a number of focal spots is generated by activating a respective number of emitters.

13. The method of claim 12, wherein the plurality of emitters further includes a first emitter with a first filament of a first emission area, and a second emitter with a second filament of a second emission area, where the first focal spot is generated by the first emitter and the second focal spot is generated by the second emitter.

14. A computed tomography (CT) system, comprising:
an X-ray tube including a cathode and a target, and an X-ray controller including one or more processors having executable instructions stored in a non-transitory memory of the CT system that, when executed, cause the one or more processors to:
create a desired distribution of electrons striking the target at each view of a subject of the CT system, the desired distribution forming a composite focal spot, the composite focal spot including a first focal spot having a first distribution of electrons striking the target based on a first configuration of electrostatic controls and/or electromagnetic controls of the X-ray controller, and a second focal spot having a second distribution of electrons striking the target based on a second configuration of electrostatic controls and/or electromagnetic controls of the X-ray controller, wherein a center of the second focal spot is separated from a center of the first focal spot;
obtain projection data from X-rays generated as a result of electrons of desired distribution of electrons striking the target; and
reconstruct an image from the projection data.

15. The system of claim 14, wherein further instructions are stored in the memory that when executed, cause the one or more processors to apply the first configuration of electrostatic controls and/or electromagnetic controls to generate the first focal spot for a first dwell time; and apply the second configuration of electrostatic controls and/or electromagnetic controls to generate the second focal spot for a second dwell time, the second dwell time starting after an end of the first dwell time.

16. The system of claim 14, wherein the first focal spot is generated by directing electrons at a first edge of the first distribution of electrons towards a center of the first distribution of electrons via the first configuration of electrostatic controls and/or electromagnetic controls, and the second focal spot is generated by directing electrons at a second edge of the second distribution of electrons towards a center of the second distribution of electrons via the second configuration of electrostatic controls and/or electromagnetic controls.

17. A method for a computed tomography (CT) system, comprising:
focusing a first beam of electrons generated by a cathode of the CT system at a first focal spot on a surface of a target of the CT system to generate a first distribution of electrons striking the target;
focusing a second beam of electrons generated by the cathode at a second focal spot on the surface of the target to generate a second distribution of electrons striking the target, wherein a center of the second focal spot is separated from a center of the first focal spot;
generating an image from projection data of the CT system acquired at a composite focal spot having a combined electron distribution that is a combination of the first distribution and the second distribution, the image including an area of focus corresponding to the composite focal spot, the area of focus including a larger area of high X-ray flux where small contrast differences between large objects are better distinguished, corresponding to the first distribution of electrons, and a smaller area of high spatial resolution where large contrast differences between small objects are better distinguished, corresponding to the second distribution of electrons.

18. The method of claim 17, wherein the first distribution and the second distribution are Gaussian distributions; and
the method further comprises applying one or more voltages to one or more focusing electrodes of the CT system to narrow and parallelize at least one of the first electron beam and the second electron beam, thereby changing the first distribution and the second distribution of electrons and increasing an intensity of the at least one of the first electron beam and the second electron beam at one or more sides of the composite focal spot, such that the composite focal spot has a large area of focus corresponding to an overall size of the composite focal spot, and a smaller area with higher spatial resolution at the one or more sides of the composite focal spot; and
further comprising obtaining projection data with the combined electron distribution.

19. The method of claim 17, wherein the first beam of electrons is generated by a first set of one or more emitters of the cathode, the second beam of electrons is generated by a second set of the one or more emitters of the cathode, and the first beam of electrons is generated concurrently with the second beam of electrons.

20. The method of claim 19, wherein generating the first beam of electrons concurrently with the second beam of electrons further includes at least one of:
initiating the first beam of electrons prior to initiating the second beam of electrons;
initiating the second beam of electrons prior to initiating the first beam of electrons;
terminating the first beam of electrons prior to terminating the second beam of electrons; and
terminating the second beam of electrons prior to terminating the first beam of electrons.

* * * * *